(12) United States Patent
Fujiwara et al.

(10) Patent No.: US 8,221,336 B2
(45) Date of Patent: Jul. 17, 2012

(54) BLOOD SENSOR AND BLOOD EXAMINING INSTRUMENT INCLUDING SAME

(75) Inventors: Masaki Fujiwara, Ehime (JP);
Toshihiro Akiyama, Ehime (JP);
Kenichi Hamanaka, Ehime (JP)

(73) Assignee: Panasonic Corporation, Osaka (JP)

( * ) Notice: Subject to any disclaimer, the term of this patent is extended or adjusted under 35 U.S.C. 154(b) by 512 days.

(21) Appl. No.: 12/441,638

(22) PCT Filed: Sep. 19, 2007

(86) PCT No.: PCT/JP2007/068151
§ 371 (c)(1),
(2), (4) Date: Mar. 17, 2009

(87) PCT Pub. No.: WO2008/035697
PCT Pub. Date: Mar. 27, 2008

(65) Prior Publication Data
US 2009/0318790 A1 Dec. 24, 2009

(30) Foreign Application Priority Data
Sep. 19, 2006 (JP) ................................ 2006-252075

(51) Int. Cl.
*A61B 5/00* (2006.01)
*A61B 5/05* (2006.01)
*B65D 81/00* (2006.01)
(52) U.S. Cl. ........................................ 600/584; 600/345
(58) Field of Classification Search .................. 600/583, 600/584, 345, 347; 606/181–183
See application file for complete search history.

(56) References Cited

U.S. PATENT DOCUMENTS

| | | | |
|---|---|---|---|
| 6,027,459 A | 2/2000 | Shain et al. | |
| 6,063,039 A | 5/2000 | Cunningham et al. | |
| 6,071,249 A | 6/2000 | Cunningham et al. | |
| 6,071,251 A | 6/2000 | Cunningham et al. | |
| 6,093,156 A | 7/2000 | Cunningham et al. | |
| 6,206,841 B1 | 3/2001 | Cunningham et al. | |
| 6,283,926 B1 | 9/2001 | Cunningham et al. | |
| 6,306,104 B1 | 10/2001 | Cunningham et al. | |
| 6,349,229 B1 | 2/2002 | Watanabe et al. | |
| 6,837,858 B2 | 1/2005 | Cunningham et al. | |
| 2004/0158137 A1* | 8/2004 | Eppstein et al. | 600/347 |
| 2004/0242982 A1 | 12/2004 | Sakata et al. | |
| 2005/0123443 A1 | 6/2005 | Fujiwara et al. | |
| 2007/0093728 A1* | 4/2007 | Douglas et al. | 600/583 |
| 2009/0043227 A1 | 2/2009 | Fujiwara et al. | |

FOREIGN PATENT DOCUMENTS

| | | |
|---|---|---|
| EP | 1426758 | 6/2004 |
| JP | 11-347018 A | 12/1999 |
| JP | 2001-515377 A | 9/2001 |
| JP | 2003-265444 A | 9/2003 |
| JP | 2005-110712 A | 4/2005 |
| WO | 2006/093206 A1 | 9/2006 |
| WO | 2007/088855 | 8/2007 |

* cited by examiner

*Primary Examiner* — Brian Szmal
(74) *Attorney, Agent, or Firm* — Greenblum & Bernstein, P.L.C.

(57) ABSTRACT

A blood sensor comprises a substrate, a spacer attached to the top of the substrate, a cover attached to the top of the spacer. A blood reservoir defined by a substrate hole formed in the substrate. A part of a spacer hole in the spacer and connected to the substrate hole, and a cover hole formed in the cover is connected to the spacer hole. A supply passage is defined by another part of the spacer hole that communicates with the blood reservoir portion, and detection electrodes are formed in the supply passage. The cover projects from the supply passage toward the inside of the blood reservoir portion farther than the substrate and the spacer.

23 Claims, 16 Drawing Sheets

BLOOD SENSOR AND BLOOD EXAMINING INSTRUMENT INCLUDING SAME

TECHNICAL FIELD

The present invention relates to a blood sensor and a blood test apparatus for performing a blood test using the blood sensor.

BACKGROUND ART

Diabetes patients need to measure the blood sugar level on a regular basis and inject insulin based on the measured blood sugar level to maintain a normal blood sugar level. To maintain this normal blood sugar level, diabetes patients need to measure the blood sugar level on a regular basis, and sample a small amount of blood from their fingertips using a blood test apparatus. A blood sensor is used to detect the blood sugar level from the sampled blood.

A conventional blood sensor will be explained using FIG. 1 to FIG. 3 (see Patent Document 1). Blood sensor 1 shown in FIG. 1 has: substrate 2 of a flat body; substrate hole 2a formed in substrate 2; a plurality of detection electrodes 3 formed in substrate 2; spacer 4 attached in the upper surface of substrate 2; spacer hole 4a that is formed in spacer 4 and that is coupled to substrate hole 2a; cover 5 attached on the upper face of spacer 4; cover hole 5a that is formed in cover 5 and that is coupled to spacer 4; blood storing part 6 formed of substrate hole 2a, spacer hole 4a and cover hole 5a; supply channel 7 with one end coupled to blood storing part 6; air hole 8 provided at the other end of supply channel 7; detecting section 9 formed of detection electrodes 3; and reagent 10 that is mounted on detecting section 9.

Blood storing part 6 of blood sensor 1 is formed with a hole that vertically penetrates blood sensor 1 of the flat body. That is, the inner diameters of substrate hole 2a, spacer hole 4a and cover hole 5a are made the same, and their center points are arranged concentrically.

With reference to FIG. 2 and FIG. 3, the operation of above blood sensor 1 will be explained.

As shown in FIG. 2A, first, blood sensor 1 attached to a blood test apparatus is made to abut on skin 11 of a patient. Next, puncturing needle 12 is launched in the direction of arrow 13. As a result, puncturing needle 12 penetrates blood storing part 6 of blood sensor 1 and punctures skin 11.

As shown in FIG. 2B, blood 15 flows out from punctured skin 11, and blood drop 15a is formed by the surface tension of outflowing blood 15. Following the outflow of blood 15, blood drop 15a becomes bigger until it contacts supply channel 7. When blood drop 15a contacts supply channel 7, blood drop 15a breaks and blood 15 flows into the interior of blood storing part 6 as shown in FIG. 2C. Then, thanks to the capillary action of supply channel 7, blood 15 is led to detecting section 9 at a burst.

In detecting section 9, blood 15 reacts with reagent 10 to produce a current proportional to the blood sugar level. To realize adequate measurement, it is necessary to stabilize the reaction with reagent 10 by making constant the speed (that is, "in the rate-controlled state") blood 15 flows into supply channel 7. The blood test apparatus measures the blood sugar level by measuring the current proportional to the blood sugar level. Based on this measured level, basic data of the dose of insulin to administer to a patient is acquired, for example.
Patent Document 1: Japanese Patent Application Laid-Open No. 2001-515377

DISCLOSURE OF INVENTION

Problems to be Solved by the Invention

With conventional blood sensor 1, for example, if blood drop 15a contacts wall 6a of blood storing part 6 on the opposite side to supply channel 7 before blood drop 15a grows to contact supply channel 7 as shown in FIG. 3, there is a possibility that blood drop 15a breaks and blood 15 flows out to upper surface 5h of cover 5. In this case, blood 15 is not supplied to supply channel 7 and the blood sugar level cannot be measured.

It is therefore an object of the present invention to provide a blood sensor that prevents such a phenomenon and supplies a sufficient amount of blood to a supply channel in a reliable manner.

Means for Solving the Problem

That is, the first of the present invention relates to a blood sensor shown below.

[1] The blood sensor according to the present invention includes: a substrate; a spacer that is attached on an upper surface of the substrate; a cover that is attached on an upper surface of the spacer; a blood storing part that is formed with a substrate hole which is formed in the substrate, a part of a spacer hole which is formed in the spacer and which is coupled to the substrate hole, and a cover hole which is formed in the cover and which is coupled to the spacer hole; a supply channel that is formed with another part of the spacer hole and that communicates with the blood storing part; and a plurality of detection electrodes formed on the supply channel. Here, the cover projects from a supply channel side toward the interior of the blood storing part, beyond the substrate and the spacer.

Further the length of projection of the cover (the length projecting beyond the substrate and spacer) is preferably made greater than the sum of the thicknesses of the substrate and spacer. Further, it is possible to apply a negative pressure to the blood storing part of the blood sensor according to the present invention through a cover hole.

Further, the blood sensor according to the present invention includes the following five modes A) to E) depending on an opening area or opening shape of a cover hole.
(A) According to the first mode, by making the opening area of the cover hole equal to or less than the opening area of the substrate hole and smaller than the opening area of the spacer hole, the cover is projected from the supply channel side toward the interior of the blood storing part, beyond the substrate and the spacer.
(B) According to the second mode, the substrate hole, the spacer hole forming the blood storing part, and the cover hole are round. Further, the diameter of the cover hole is made equal to or less than the diameter of the substrate hole and is shorter than the diameter of the spacer hole. By arranging the centers of the substrate hole, the spacer hole and the cover hole concentrically, the cover is projected from the supply channel side toward the interior of the blood storing part, beyond the substrate and the spacer.
(C) According to the third mode, the substrate hole, the spacer hole, and the cover hole are round. Further, the diameter of the cover hole is made equal to or less than the diameter of the substrate hole and shorter than the diameter of the spacer hole. By arranging the centers of the spacer hole and the cover hole concentrically and arranging the center of the substrate hole farther away from the supply channel than the center of the spacer hole, the cover is projected from the supply channel side toward the interior of the blood storing part, beyond the substrate and the spacer.

(D) According to the fourth mode, the substrate hole, the spacer hole, and the cover hole are round. Further, the diameter of the substrate hole is made longer than the diameter of the cover hole and equal to the diameter of the spacer hole. The centers of the substrate hole and the spacer hole are arranged concentrically and the center of the cover hole is arranged farther away from the supply channel than the center of the substrate hole. With this configuration, the cover is projected from the supply channel side toward the interior of the blood storing part, beyond the substrate and the spacer.

(E) According to the fifth mode, by forming in the cover a projecting part projecting from the supply channel side toward the interior of the blood storing part, the cover is projected from the supply channel side toward the interior of the blood storing part, beyond the substrate and the spacer. By projecting part of the cover by providing a projecting part, blood inside the blood storing part is less likely to be led to other than the periphery of the supply channel compared to the case where the cover is projected from the entire periphery of the blood storing part. Consequently, it is possible to reduce the amount of blood that is required to sample.

Further, preferably, the substrate of the blood sensor according to the present invention is projected from the supply channel side toward the interior of the blood storing part, beyond the spacer. However, the length of projection of the substrate is preferably smaller than the length of projection of the cover. Projecting both of the substrate and cover forms the space between the substrate and cover that communicates with the supply channel. Accordingly, when capillary force is produced in this space, it is possible to lead blood of the blood storing part to the supply channel in a more reliable manner.

Further, in the blood sensor according to the present invention, the substrate, the spacer and the cover form a base plate of a polygon (preferably, a regular polygon), and electrodes may be provided at the apexes of the polygon. Furthermore, the electrodes provided at the apexes are each connected with one of the detection electrodes, and two electrodes among the electrodes provided at the apexes are connected with the same detection electrode. Based on one of the two electrodes connected with the same detection electrode, it is possible to specify with which detection electrode each electrode provided at each apex of the polygon is connected. Further, the base plate is a hexagon (preferably, regular hexagon).

In the blood sensor according to the present invention, water-repellency or hydrophobicity of the surface of each member may be adjusted, so that it is possible to smoothly lead blood to the detecting section of the supply channel.

For example, in the blood sensor according to the present invention, it is possible to make the upper surface of the cover water-repellent and the inner surface of the supply channel hydrophilic, and make the ceiling of the blood storing part less hydrophilic than the inner surface of the supply channel or less water-repellent than the upper surface of the cover. Further, the lower surface of the substrate of the blood sensor according to the present invention may be made water-repellent.

The second of the present invention relates to a blood test apparatus that has the blood sensor explained below. The blood test apparatus according to the present invention can be roughly divided into the following two modes of [2] and [3] depending on the puncturing means.

[2] According to the first mode, a blood test apparatus includes: a housing; a cylinder body that is formed at one end of the housing; a plunger that moves back and forth inside the cylinder body; a lancet that is held at one end by the plunger detachably and has at the other end a puncturing needle attached; a blood sensor that is provided facing the puncturing needle; and an electrical circuit section that is connected with the blood sensor, and the blood sensor is a blood sensor according to above [1].

[3] According to the second mode, a blood test apparatus includes: a housing; a cylinder body that is formed at one end of the housing; a laser emitting apparatus that is provided inside the cylinder body; a blood sensor that is provided facing a laser emitting opening of the laser emitting apparatus; and an electrical circuit section that is connected with the blood sensor, and the blood sensor is a blood sensor according to above [1].

In the blood test apparatus according to the present invention, the blood sensor may be made as a cartridge. That is, the blood sensor is attached to a cylindrical holder to make a cartridge, and the cartridge is attached removably to the cylinder body of the blood test apparatus according to the present invention. The holder of the cartridge may be formed of a transparent or semitransparent member such that the interior can be seen.

In the blood test apparatus according to the present invention, negative pressure means that applies a negative pressure near the blood sensor may be provided. The negative pressure means can apply a negative pressure near the blood sensor.

The puncturing means of the blood test apparatus according to the present invention preferably punctures a skin at a position closer to a supply channel side than the center of a cover hole formed in the blood sensor. As described above, the puncturing means may be a puncturing needle or laser light.

Advantageous Effect of the Invention

The blood sensor according to the present invention makes it possible to lead a small amount of blood sampled in a blood storing part, to a detecting section arranged in a supply channel in a reliable manner. Consequently, the blood test apparatus having the blood sensor according to the present invention makes it possible to perform a more adequate blood test.

Further, a cover hole that forms a blood storing part is provided in the cover of the blood sensor according to the present invention, so that energy to break through the cover is not required upon puncturing. Consequently, stable puncturing is possible. Further, a negative pressure can also be supplied through this cover hole, so that it is possible to accelerate vacuuming.

BRIEF DESCRIPTION OF DRAWINGS

FIG. 6 is an exploded plan view of components forming the blood sensor according to Embodiment 1;

BEST MODE FOR CARRYING OUT THE INVENTION

1. Regarding the blood sensor according to the present invention.

The blood sensor according to present invention has a cover, spacer and substrate. Each member is preferably formed in a flat shape and stacked upon one another. That is, a spacer is stacked on a substrate, and, further, a cover is stacked on the spacer. The material of the cover, spacer and substrate is not limited in particular and may be polyethylene terephthalate (PET), for example.

The thickness of the substrate is preferably between 75 micrometers and 250 micrometers (for example, 100 micrometers), the thickness of the spacer is preferably between 50 micrometers and 150 micrometers (for example, 50 micrometers) and the thickness of the cover is preferably between 50 micrometers and 250 micrometers (for example, 75 micrometers).

The holes (penetrating holes) formed in the cover, spacer and substrate are referred to as the "cover hole," "spacer hole" and "substrate hole," respectively. The cover hole, part of the spacer hole and the substrate hole communicate with each other and form the blood storing part of the blood sensor. The volume of the blood storing part is preferably between 0.2 and 6.5 microliters, approximately.

Further, although one part of the spacer hole forms the blood storing part, the other part forms a supply channel communicating with the blood storing part. The supply channel is preferably in size of a micro-channel where capillary action is produced, and so the other part of the spacer hole is preferably formed in a slit shape. The volume of the supply channel is preferably between 0.02 and 0.75 microliters, (for example, 0.072 microliters), approximately.

Further, the ratio of the volume of the blood storing part to the volume of the supply channel is preferably 5~10:1.

Figure 1:
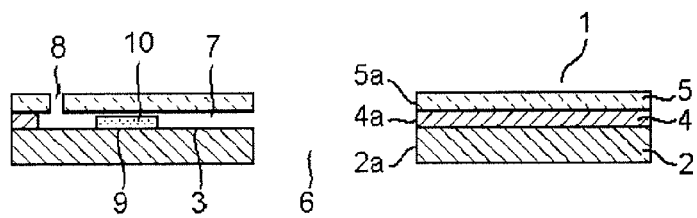
FIG. 1 is a cross-sectional view showing a conventional blood sensor.
Figure 2A:
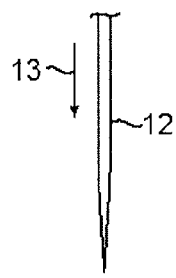
FIG. 2A is a cross-sectional view of the blood sensor of FIG. 1 and shows a state before needle puncturing is performed.
Figure 2A:
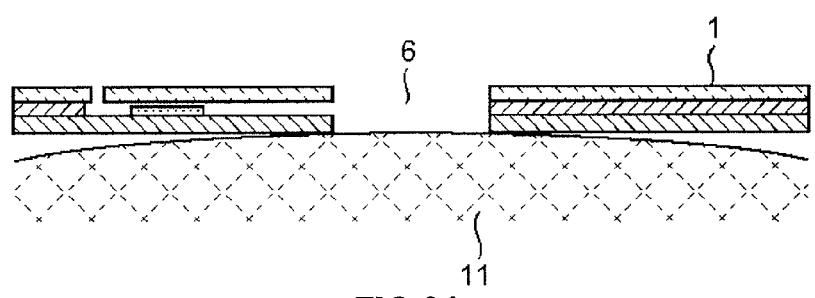
Figure 2B:
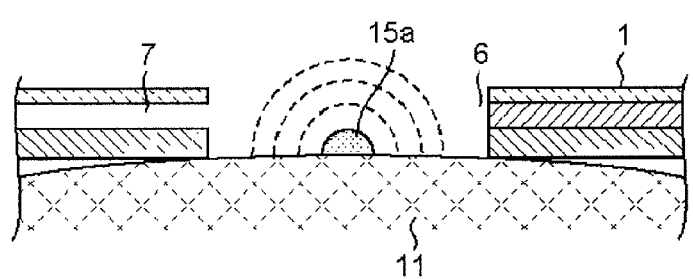
FIG. 2B is a cross-sectional view of a blood sensor of FIG. 1 and shows a state where a drop of blood grows from the part to be punctured.
Figure 2C:
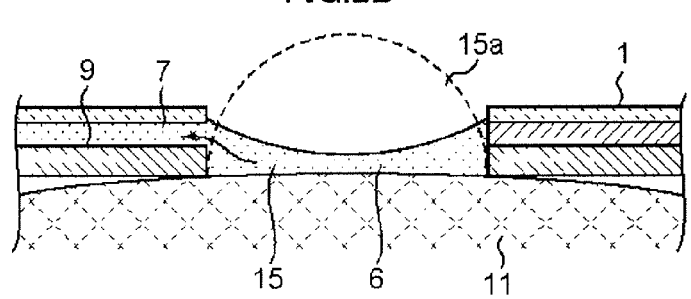
FIG. 2C is a cross-sectional view of the blood sensor of FIG. 1 and shows a state where blood flows into a supply channel from a blood storing part.
Figure 3:
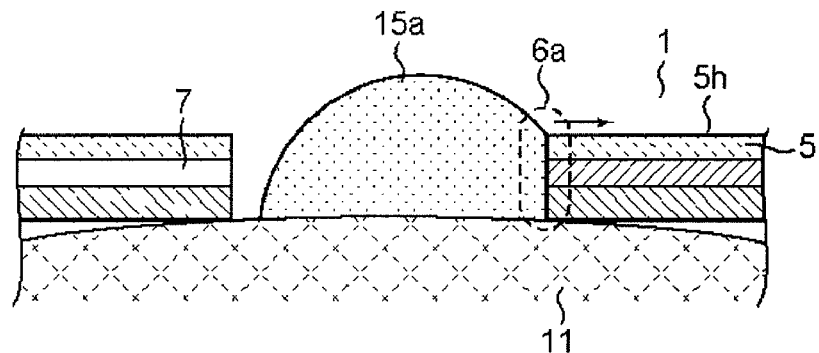
FIG. 3 is a cross-sectional view of the blood sensor of FIG. 1 and shows a state of uncommon use where blood does not flow into the supply channel from the blood storing part.
Figure 4:
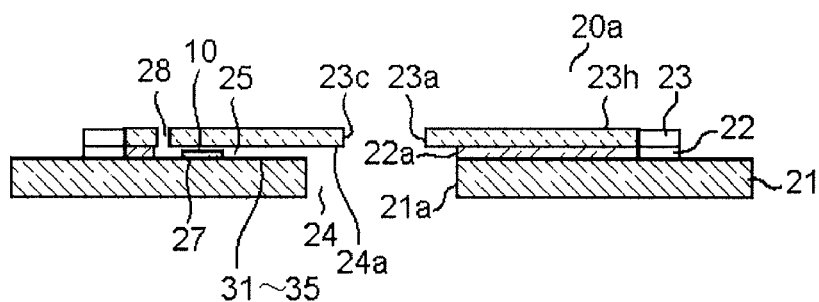
FIG. 4 is a cross-sectional view of the blood sensor according to Embodiment 1.

The substrate hole, spacer hole and cover hole communicate to form the blood storing part, and so the blood storing part is open on the substrate side and the cover side (see FIG. 4, for example). The skin puncturing means (i.e. a puncturing needle or laser light) punctures skin from the spacer side through the blood storing part, and the blood flowing out from skin is guided into the blood storing part from the opening of the substrate side.

In this way, the blood storing part is open on the substrate side and on the cover side, so that it is possible to apply a negative pressure to the interior of the blood storing part through the spacer hole. By applying a negative pressure to the interior of the blood storing part, skin is suctioned before puncturing and the outflowing blood is efficiently led to the blood storing part.

Although the shape of each hole forming the blood storing part is not limited in particular, the blood storing part is characterized by projecting the cover beyond the substrate and spacer toward the interior of the blood storing part from the side where a supply channel of the blood sensor is provided. That is, in the blood storing part of the blood sensor, the cover projects beyond the substrate and spacer toward the interior of the blood storing part.

A cover (1) may project from the entire periphery of the cover hole toward the interior of the blood storing part (see FIG. 7, FIG. 9 and FIG. 11) or (2) may selectively project toward the interior of the blood storing part from the side where the supply channel of the blood sensor is provided (see FIG. 14 and FIG. 16).

From the side where the supply channel is provided toward the interior of the blood storing part, the cover preferably projects more than the sum of the thicknesses of the substrate and spacer, beyond the substrate and spacer. As described below, the projecting part of the cover first contacts blood flowing out from punctured skin and stored in the blood storing part, so that it is possible to lead blood to the supply channel in a reliable manner. Further, when the cover projects more than the sum of the thicknesses of the substrate and spacer, beyond the substrate and spacer toward the interior of the blood storing part, blood inside the blood storing part can contact the projecting part of the cover in a more reliable manner. Further, although the cover only needs to project beyond the substrate and spacer, the upper limit of the length of projection is preferably equal to or less than 2 millimeters.

To project a cover from the side where the supply channel is provided toward the interior of the blood storing part, first, it is considered to make the opening area of the cover hole smaller than the opening area of the substrate hole and the opening area of the spacer hole forming the blood storing part (see Embodiment 1). In a case where the holes are formed in random similar shapes (for example, round, oval, polygon or pentagon) and the centers or gravity centers are arranged concentrically, it is possible to project the cover toward the interior of the blood storing part by making the opening area of the cover hole smaller.

To project the cover from the side where the supply channel is provided toward the interior of the blood storing part, it is also possible to provide with the cover the projecting part which extends from the supply channel side toward the interior of the blood storing part (see Embodiment 5). In this case, it is possible to make only the cover near the supply channel project selectively.

To project the cover from the side where the supply channel is provided toward the interior of the blood storing part, it is also possible to form the substrate hole, spacer hole and cover hole in a round shape and adjust the inner diameters and locations of the centers (see Embodiments 2 to 4).

Further, the cover may be projected from the side where the supply channel is provided toward the interior of the blood storing part, and the substrate may be projected toward the interior of the blood storing part from the side where the supply channel is provided. However, the length of projection of the cover is made longer than the length of projection of the substrate. At this point, capillary force is produced in the space formed between the cover and the substrate, so that blood in the blood storing part is more likely to be led to this space. This space communicates with the supply channel, so that it is possible to supply blood to the supply channel in a more reliable manner.

For example, when the diameter of the cover hole is made equal or smaller than the diameter of the substrate hole and is made smaller than the diameter of the spacer hole, the cover uniformly projects from the entire periphery of the cover hole toward the interior of the blood storing part by (1) concentrically arranging the center of each hole (see Embodiment 2) or by (2) arranging the centers of the cover hole and the spacer hole concentrically and arranging the center of the substrate hole at a position farther away from the supply channel than the center of the cover hole (see Embodiment 3).

With Embodiment 2, the groove formed by the substrate and the cover is formed uniformly in the periphery of the blood storing part. On the other hand, with Embodiment 3, the groove formed by the substrate and cover is formed mainly on the supply channel side.

Further, when the diameter of the substrate hole is made greater than the diameter of the cover hole and made equal to the diameter of the spacer hole, the centers of the substrate hole and spacer hole are arranged concentrically and the center of the cover hole is arranged at a position farther away from the supply channel than the center of the substrate hole. With this configuration, the cover is projected from the supply channel side toward the interior of the blood storing part, and the projection from the opposite side to the supply channel can be eliminated or reduced (see Embodiment 4).

Further, in the supply channel formed of other parts of the spacer hole (a hole in a slit shape), two or more detection electrodes for detecting the components of blood supplied to the supply channel, are arranged. A detection electrode includes a pair of electrodes consisting of an "active electrode" and a "counter electrode." The "active electrode" refers to an electrode for detecting blood components, and the "counter electrode" refers to an electrode that makes a pair with the active electrode. Further, the detection electrode preferably includes a "sensing electrode," which is an electrode for detecting whether or not blood is supplied to the detecting section. The detection electrode may include an "Hct electrode" for measuring the hematocrit level in blood.

Each detection electrode arranged in the supply channel is connected with a connection electrode for connecting with an external circuit (a circuit of the blood measuring apparatus). The mode of the connection electrode is not particularly limited as long as the connection electrode can be connected with the external circuit, and, for example, the connection electrode is arranged in the end part of the blood sensor.

Further, by forming the blood sensor in a polygon (preferably, a regular polygon), connection electrodes may be arranged at the apexes of this polygon.

Further, one detection electrode may be connected to two connection electrodes. The potential difference between two connection electrodes connected to one detection electrode is zero. Consequently, it is possible to specify each detection electrode based on one of the detected connection electrodes by detecting connection electrodes of the potential difference of zero. In this way, the connection electrodes based on which each detection electrode is specified, are referred to as "reference electrodes."

For example, the blood sensor may be made as a regular hexagon. In this case, it is preferable that six connection electrodes be arranged and four or five detection electrodes be arranged. In a case where four detection electrodes are arranged, the detection electrodes preferably include an active electrode, counter electrode, sensing electrode and Hct electrode, and two reference electrodes are arranged. In a case where five detection electrodes are arranged, the detection electrodes preferably include an active electrode, counter electrode, two sensing electrodes and Hct electrode, and one reference electrode is arranged.

A reagent that reacts with the blood components of interest may be arranged on at least part of two or more detection electrodes (for example, "active electrode" and "counter electrode") included in the blood sensor of the present invention. The reagent is selected appropriately depending on the blood components of interest and, for example, to measure the blood sugar level, the reagent may be a mixture of PQQ-GDH and potassium ferricyanide.

The blood sensor according to the present invention is used in combination with a blood test apparatus for a blood test. The blood sensor is preferably made as a cartridge to be attached to the blood test apparatus removably. For example, the cartridge is formed of the blood sensor and a cylindrical holder attached with the blood sensor. The cylindrical holder may be provided with a mechanism for attaching to the blood test apparatus. Further, when at least part of the cylindrical holder is made transparent or semi-transparent to visually check (see through) the interior of the blood sensor, how blood is sampled can be observed, which is preferable.

Specific examples of the blood test apparatus incorporating the blood sensor of the present invention will be explained in Embodiments 6 and 7, and a puncturing needle or laser radiating device is preferably included as the puncturing means for puncturing skin and letting blood flow out. The puncturing means punctures skin penetrating the blood storing part of the blood sensor, and the part to be punctured is preferably closer to the supply channel than the center of the cover hole. By setting the part to be punctured close to the supply channel, blood is more likely to contact the cover projecting part projecting from the supply channel side toward the interior of the blood storing part. Consequently, blood is led to the supply channel in a more reliable manner.

The blood test apparatus according to the present invention may include a negative pressure means that applies a negative pressure near the blood sensor. By applying the negative pressure near the blood sensor to apply negative pressure in the blood storing part through the cover hole, it is possible to suction skin to be punctured. Blood readily flows out from the skin which is suctioned to be lifted up, so that a blood test becomes more reliable.

Embodiment 1

FIG. 4 to FIG. 8 show an example of a blood sensor (Embodiment 1) according to the present invention.

FIG. 4 is a cross-sectional view of blood sensor 20*a* according to Embodiment 1. Blood sensor 20*a* has a plate shape and is formed of: substrate 21; spacer 22 pasted on the upper surface of substrate 21; and cover 23 pasted on the upper surface of spacer 22.

Blood storing part 24 is a space which substrate hole 21*a* formed at approximately the center of substrate 21; spacer hole 22*a* formed at approximately the center of spacer 22 and cover hole 23*a* formed at approximately the center of cover 23 communicate to form. Blood storing part 24 is open downward and upward.

By making the lower surface of substrate 21 of blood sensor 20*a* abut on skin and puncturing the skin inside the blood storing part, blood from the skin is stored in blood storing part 24. One end of supply channel 25 is coupled to blood storing part 24 and the other end is coupled to air hole 28 formed in the cover. The blood stored in blood storing part 24 is led by capillary action to detecting section 27 (see FIG. 5) formed on supply channel 25.

It is preferable to prevent blood stored in blood storing part 24 from leaking through cover hole 23*a* by making upper surface 23*h* of cover 23 water-repellant. Further, it is preferable to make blood stored in blood storing part 24 flow into supply channel 25 in a simple manner by making the inner surface of supply channel 25 hydrophilic.

Further, ceiling 24*a* of blood storing part 24 is preferably made less hydrophilic than the inner surface of supply channel 25 or less water-repellent than upper surface 23*h* of cover 23. With this configuration, it is possible to prevent blood stored in blood storing part 24 from leaking from cover hole 23*a*, and accelerate inflow of blood into supply channel 25.

Further, the lower surface of substrate 21 (i.e. contact surface with skin) is preferably made water-repellent so as not to let blood flowing out from punctured skin flow out from blood storing part 24.

Here, as for "water-repellency," the surface free energy is preferably less than 43 mN/m. The means for making the surface of each member water-repellent or hydrophilic is not limited in particular. For example, each member may be formed using a water-repellent material or hydrophilic material, and the surface of each member may be treated with a water-repellent agent or hydrophilizing agent.

Reagent 10 mounted on detecting section 27 is selected as appropriate according to the types of blood components to be measured. For example, when the blood sugar level is measured, reagent 10 may be a mixture of PQQ-GDH and potassium ferricyanide. Reagent 10 can be prepared by dropping on detection electrode 31 and detection electrode 33 (see FIG. 5) formed on substrate 21*a* reagent solution, prepared by dissolving PQQ-GDH and potassium ferricyanide to an aqueous solution of CMC, and drying the reagent solution.

Figure 5:
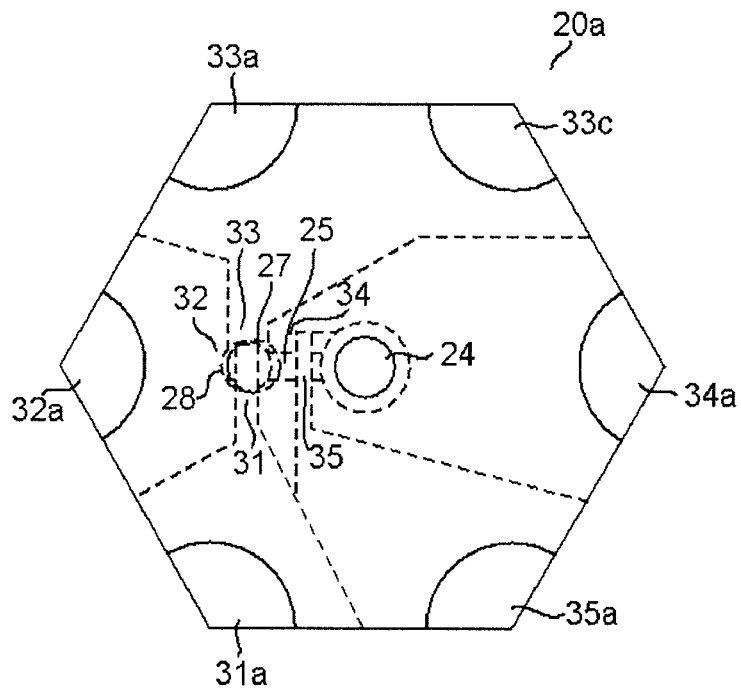
FIG. 5 is a perspective plan view of the blood sensor according to Embodiment 1.

FIG. 5 is a perspective plan view of blood sensor 20*a*. The shape of blood sensor 20*a* from a plan view is a regular hexagon. Connection electrodes 31*a* to 35*a* and 33*c* are formed at the six apexes of the regular hexagon, and connection electrode 33*c* operates as a reference electrode. That is, connection electrodes 33*a* and 33*c* are electrically connected, and, by this means, connection electrode 33*c* operates as a reference electrode (hereinafter, "reference electrode 33*c*"). The reference electrode will be explained in detail below. Connection electrodes 31*a* to 35*a* and 33*c* (i.e. reference electrode) are connected with a connector of the blood test apparatus (described later).

Supply channel 25 is provided such that its one end is connected with blood storing part 24 provided at approximately the center of blood sensor 20*a*. Supply channel 25 extends from blood storing part 24 toward connection electrode 32a and the other end of supply channel 25 is coupled to air hole 28.

From the side closer to blood storing part 24, "detection electrode 34 connected with connection electrode 34a," "detection electrode 35 connected with connection electrode 35a," again "detection electrode 34 connected with connection electrode 34a," "detection electrode 33 connected with connection electrode 33a and reference electrode 33c," "detection electrode 31 connected with connection electrode 31a," again "detection electrode 33 connected with connection electrode 33a and reference electrode 33c" and "detection electrode 32 connected with connection electrode 32a," are provided on supply channel 25.

Reagent 10 is mounted on detection electrode 31 and detection electrode 33 to form detecting section 27.

Figure 6A:
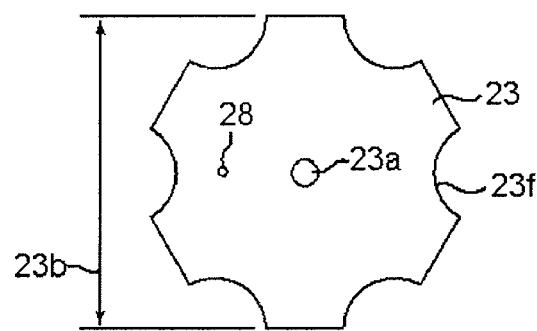
FIG. 6A is a plan view of a cover.
Figure 6B:
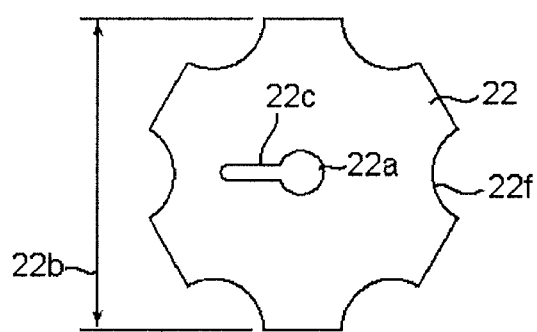
FIG. 6B is a plan view of a spacer.
Figure 6C:
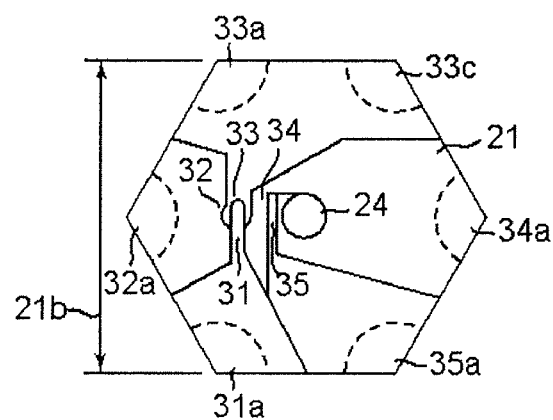
FIG. 6C is a plan view of a substrate.

FIG. 6 is an exploded plan view of blood sensor 20a. FIG. 6C is a plan view of regular hexagonal substrate 21 forming blood sensor 20a. Dimension 21b of substrate 21 is 9 millimeters. The material of substrate 21 is polyethylene terephthalate (PET) and the thickness of substrate 21 is 100 micrometers.

On the upper surface of substrate 21, detection electrodes 31 to 35 and connection electrodes 31a to 35a and reference electrode 33c extended from detection electrodes 31 to 35 are arranged. The electrodes may be formed integrally by laser processing of a conductive layer deposited on substrate 21 by sputtering or vapor deposition. The raw material of the conductive layer is, for example, gold, platinum or palladium. Further, substrate hole 21a is provided at approximately the center of substrate 21.

FIG. 6B is a plan view of spacer 22. The material of spacer 22 is polyethylene terephthalate and the thickness of spacer 22 is 50 micrometers.

Spacer 22 is a regular hexagon having semicircular cutouts 22f at the six apexes. The cutouts at the apexes of the regular hexagon are formed in positions meeting connection electrodes 31a to 35a and reference electrode 33c of substrate 21. Dimension 22b is 9 millimeters. Holes are formed in spacer 22, including spacer hole 22a and slit hole 22c. Spacer hole 22a is at a position meeting substrate hole 21a and is provided at approximately the center of spacer 22, and forms part of the blood storing part.

Slit hole 22c formed in spacer 22 communicates with spacer hole 22a and forms supply channel 25 of blood 15. Consequently, the wall surface of slit hole 22c and the upper surface of substrate 21 meeting slit hole 22c are preferably subjected to hydrophilic treatment. The width of slit hole 22c is 0.6 millimeters and the length of slit hole 22c is 2.4 millimeters. With this configuration, supply channel 25 includes a cavity of 0.072 microliters. Consequently, a blood test by the blood sensor according to the present invention can be performed with a little amount of blood 15, so that the patient does not need to bear burden and scare.

FIG. 6A is a plan view of cover 23. The material of cover 23 is polyethylene terephthalate and the thickness of cover 23 is 75 micrometers. Dimension 23b of cover 23 is 9 millimeters. Cover hole 23a is provided at approximately the center of cover 23. Air hole 28 is provided to meet the tip part of supply channel 25 (corresponding to the left end part of slit 22c in FIG. 6B). Diameter 28a of air hole 28 is between 50 and 500 micrometers (for example, 50 micrometers). The diameter of air hole 28 is shortened to prevent blood 15 from flowing out from air hole 28.

Cover 23 is a regular hexagon having semicircular cutouts 23f at the six apexes. The cutouts at the apexes of the regular hexagon in cover 23 are formed at positions meeting connection electrodes 31a to 35 and reference electrode 33c of substrate 21.

Substrate 21, spacer 22 and cover 23 forming blood sensor 20a can be formed by dividing parent substrates of fixed measures into several pieces. Substrate 21, spacer 22 and cover 23 to be divided are made as regular hexagons and, consequently, can be cut out from the parent substrates without producing space. Consequently, it is possible to acquire each member from the parent substrates without waste, contributing to saving resources.

Figure 7:
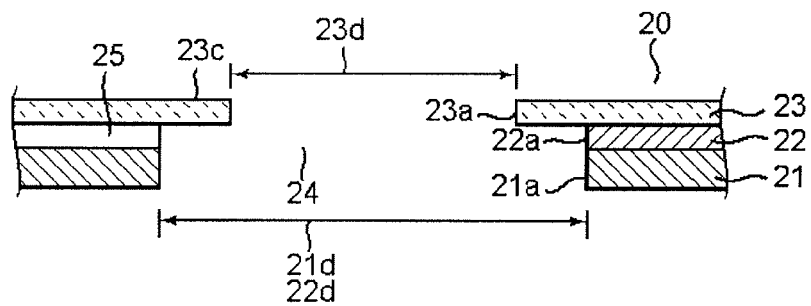
FIG. 7 is a cross-sectional view of the blood storing part of the blood sensor according to Embodiment 1.

FIG. 7 is a cross-sectional view of blood storing part 24 according to Embodiment 1 and its vicinity. The thickness of substrate 21 is 100 micrometers and the thickness of spacer 22 is 50 micrometers. Further, the thickness of cover 23 is 75 micrometers.

Diameter 21d of substrate hole 21a and diameter 22d of spacer hole 22a are each 2.0 millimeters and diameter 23d of cover hole 23a is 1.5 millimeters. Substrate hole 21a, spacer hole 22a and cover hole 23a are formed concentrically. That is, there are the centers of substrate hole 21a, spacer hole 22a and cover hole 23a along the center axis of blood storing part 24.

Diameter 22d of spacer hole 22a is greater than diameter 23d of cover hole 23a and diameter 22d of spacer hole 22a and diameter 21d of substrate hole 21a are equal.

Diameter 23d of cover hole 23a is smaller than the diameters of substrate hole 21a and spacer hole 22a, so that cover 23 projects toward the interior of blood storing part 24 to form projecting part 23c. The length of projection of projecting part 23c of blood sensor 20a (250 micrometers) is 100 micrometers greater than the sum of thicknesses of substrate 21 and spacer 22 (150 micrometers). By providing such projecting part 23c, it is possible to let blood drop 15a sampled inside blood storing part 24 flow into supply channel 25 before reaching the contact point between blood storing part 24 and skin 11 (see the dotted-line circles in FIG. 8B). Accordingly, the length of projection of projecting part 23c formed by cover 23 is preferably greater than the sum of thicknesses of substrate 21 and spacer 22.

Figure 8A:
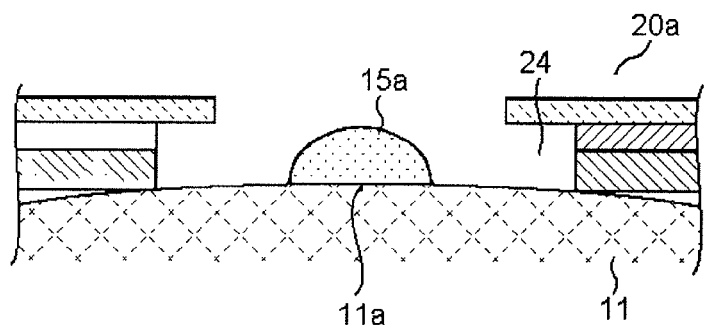
FIG. 8A is a cross-sectional view of the blood storing part of the blood sensor according to Embodiment 1 and shows a state where the drop of blood flowing out from punctured skin is formed.

The state where blood 15 flows into supply channel 25 will be explained with reference to FIG. 8A to FIG. 8C. As shown in FIG. 8A, when skin 11 inside blood storing part 24 is punctured, blood 15 flows out from punctured hole 11a to form blood drop 15a.

Figure 8B:
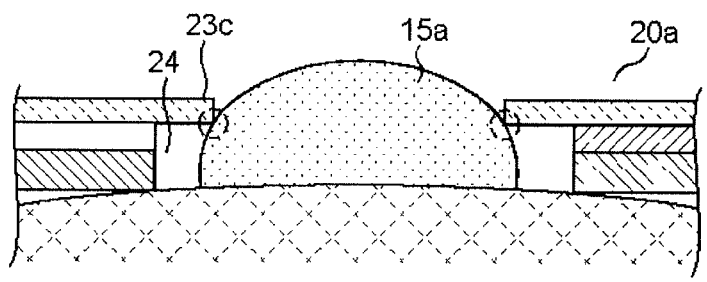
FIG. 8B is a cross-sectional view of the blood storing part of the blood sensor according to Embodiment 1 and shows a state where the drop of blood flowing out from punctured skin grows to contact a projecting part of the cover hole.
Figure 8C:
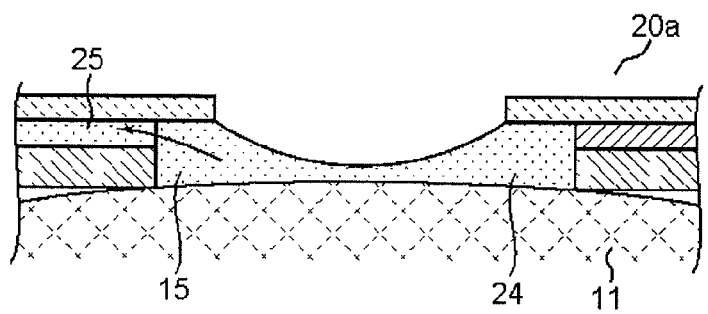
FIG. 8C is a cross-sectional view of the blood storing part of the blood sensor according to Embodiment 1 and shows a state where blood flows into the supply channel from the blood storing part.

Blood drop 15a becomes bigger due to the outflow of blood 15 from punctured hole 11a and contacts projecting part 23c as shown in FIG. 8B. Then, as shown in FIG. 8C, blood 15 forming blood drop 15a spreads in blood storing part 24 and flows into supply channel 25 at a burst. That is, a sufficient amount of blood 15 stored in blood storing part 24 is supplied to supply channel 25 at a burst, so that blood 15 flows into supply channel 25 in a state of a constant speed (rate-controlled state). As a result, the reaction with reagent 10 (see FIG. 4) does not stop halfway due to lack of blood 15, or reagent 10 is not swept away from detecting section 27 due to an excess of blood 15 such that the reaction occurs in places except in detecting section 27. Therefore, the reaction with reagent 10 occurs in a predetermined part at a constant rate of reaction at all times. Consequently, it is possible to obtain a precise and stable measurement result.

Embodiment 2

FIG. 9 and FIG. 10 show blood sensor 20b according to Embodiment 2.

Blood sensor 20b differs from blood sensor 20a according to Embodiment 1 in forming groove 26a between substrate 21 and cover 23. This difference will be mainly explained below, and the same members as in Embodiment 1 will be assigned the same reference numerals and explanation thereof will be simplified.

Figure 9A:
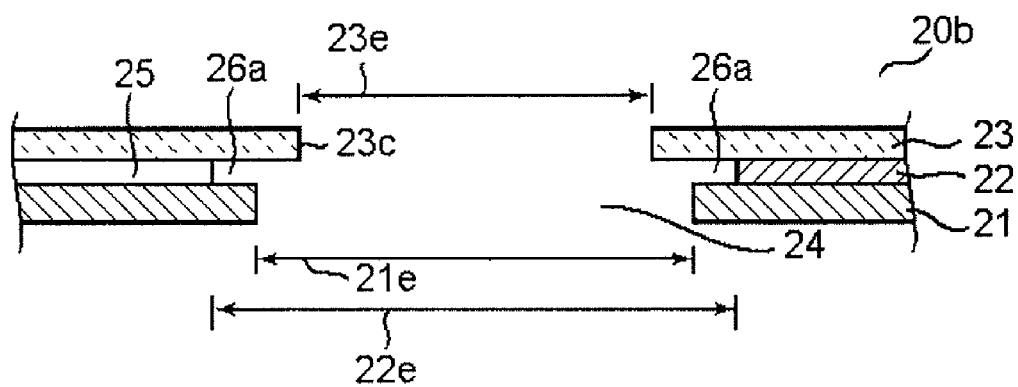
FIG. 9A is a cross-sectional view of the blood storing part of the blood sensor according to Embodiment 2.
Figure 9B:
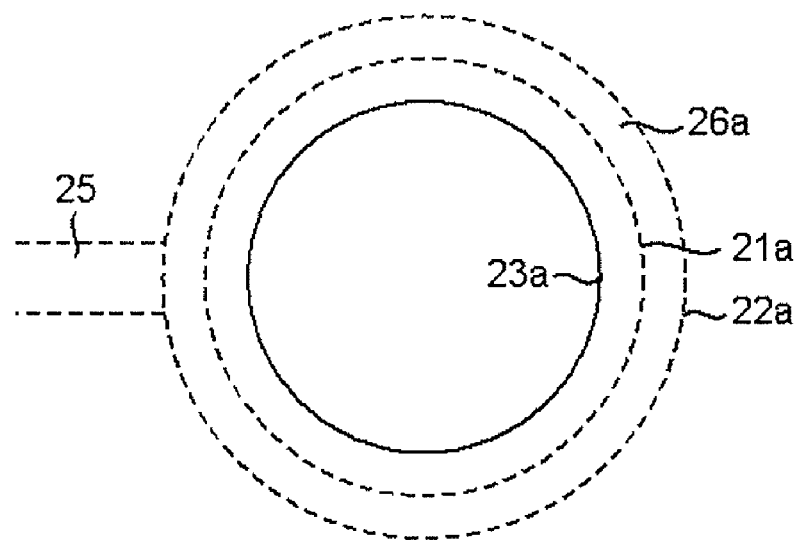
FIG. 9B is a perspective plan view of the blood storing part of the blood sensor according to Embodiment 2.

FIG. 9A is a cross-sectional view of blood storing part 24 of blood sensor 20b and its vicinity and FIG. 9B is its perspective plan view. Diameter 21e of substrate hole 21a formed in substrate 21 is 1.6 millimeters. Diameter 22e of spacer hole 22a formed in spacer 22 is 2.0 millimeters. Further, diameter 23e of cover hole 23a formed in cover 23 is 1.0 millimeters. The centers of substrate hole 21a, spacer hole 22a and cover hole 23a are concentric.

Similar to Embodiment 1, in blood storing part 24 of blood sensor 20b, cover 23 projects toward the center of blood storing part 24 to form projecting part 23c. The length of projection of projecting part 23c (200 micrometers) is greater than the sum of thicknesses of substrate 21 and spacer 22 (150 micrometers). Consequently, similar to Embodiment 1, thanks to projecting part 23c, it is possible to let blood drop 15a sampled in blood storing part 24 flow into supply channel 25 before reaching the contact point between blood storing part 24 and skin 11.

As shown in FIG. 9A, groove 26a is formed between substrate 21 and cover 23 of blood storing part 24. Groove 26a has a ring shape as shown in FIG. 9B, the inner diameter of 1.6 millimeters, the external diameter of 2.0 millimeters, the width of 200 micrometers and the height of 50 micrometers (the same thickness as spacer 22).

The centers of substrate hole 21a, spacer hole 22a and cover hole 23a are positioned along the center axis of blood storing part 24. Diameter 21e of substrate hole 21a is greater than diameter 23e of cover hole 23a and diameter 22e of spacer hole 22a is greater than diameter 21e of substrate hole 21a.

Figure 10A:
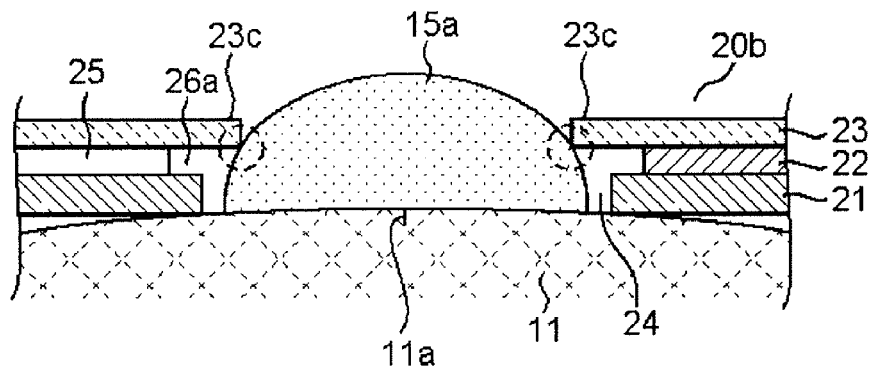
FIG. 10A is a cross-sectional view of the blood storing part of the blood sensor according to Embodiment 2 and shows a state where the drop of blood flowing out from punctured skin contacts the projecting part of the cover hole.
Figure 10B:
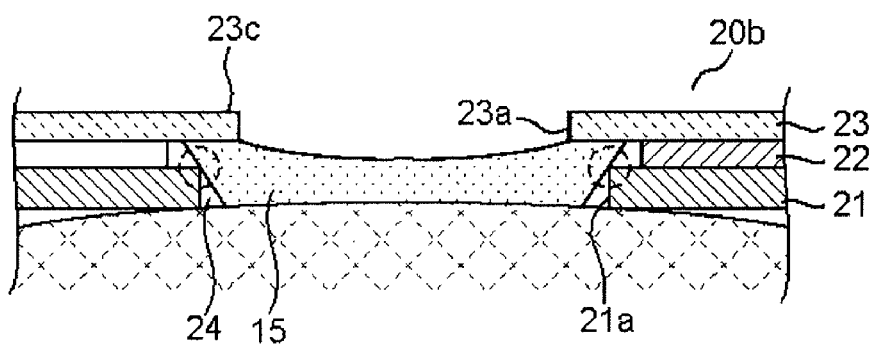
FIG. 10B is a cross-sectional view of the blood storing part of the blood sensor according to Embodiment 2 and shows a state where blood flows into the supply channel from the blood storing part.
Figure 10C:
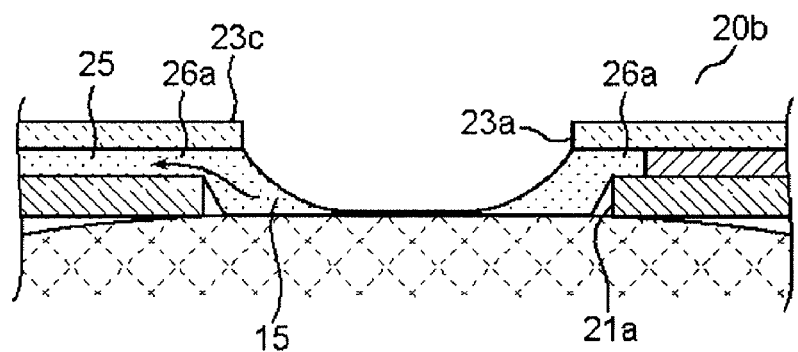
FIG. 10C is a cross-sectional view of the blood storing part of the blood sensor according to Embodiment 2 and shows a state after blood in the blood storing part flows into the supply channel.

The operation of sampling blood by blood sensor 20b will be explained with reference to FIG. 10. When skin 11 inside blood storing part 24 is punctured, blood 15 flows out from punctured hole 11a to form blood drop 15a. As shown in FIG. 10A, when blood drop 15a becomes bigger, blood drop 15a abuts on the tips of projecting part 23c (shown by dotted-line circles). Then, as shown in FIG. 10B, blood drop 15a tries to spread inside blood storing part 24 at a burst. Spreading blood 15 abuts on the tips of substrate hole 21a of the spacer side (FIG. 10B) shown by dotted-line circles. Capillary force is produced in groove 26a, so that, as shown in FIG. 10C, blood 15 flows into groove 26a at a burst, and, further, blood 15 that has flowed into groove 26a flows into supply channel 25 in a rate-controlled state.

In this way, thanks to the capillary force produced in groove 26a, it is possible to let blood 15 flow into detecting section 27 through supply channel 25 (see FIG. 4) in a more reliable manner. Further, the amount of blood left in blood storing part 24 after a test is less than that of blood sensor 20a according to Embodiment 1. Consequently, blood 15 to be sampled decreases accordingly and burden on patients is reduced.

Embodiment 3

FIG. 11 and FIG. 12 show blood sensor 20C according to Embodiment 3.

Groove 26b similar to groove 26a of blood sensor 20b according to Embodiment 2 is formed between substrate 21 and cover 23 of blood sensor 20c. However, groove 26b differs from groove 26a in that groove 26b is formed on the supply channel 25 side and is not formed on opposite side 24e to supply channel 25. This difference will be mainly explained below, and the same members as blood sensor 20b according to Embodiment 2 will be assigned the same reference numerals and explanation thereof will be simplified.

Figure 11A:
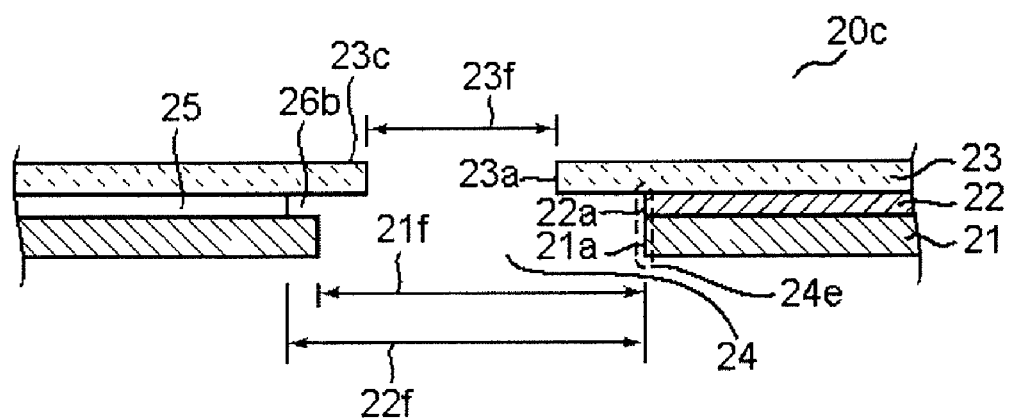
FIG. 11A is a cross-sectional view of the blood storing part of the blood sensor according to Embodiment 3.
Figure 11B:
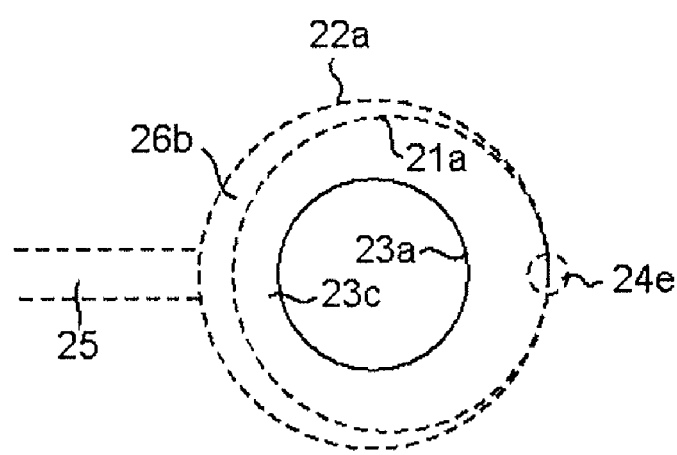
FIG. 11B is a perspective plan view of the blood storing part of the blood sensor according to Embodiment 3.

FIG. 11A is a cross-sectional view of blood storing part 24 of blood sensor 20c and its vicinity and FIG. 11B is its perspective plan view. Diameter 21f of substrate hole 21a formed in substrate 21 is 1.8 millimeters. Diameter 22f of spacer hole 22a formed in spacer 22 is 2.0 millimeters. Further, diameter 23f of cover hole 23a formed in cover 23 is 1.0 millimeters.

The centers of spacer hole 22a and cover hole 23a are concentric and the center of substrate hole 21a is at a position farther away from supply channel 25 than those concentric centers. Consequently, on opposite side 24e to supply channel 25, substrate hole 21a and spacer hole 22a are aligned, and no groove is formed between substrate 21 and cover 23.

In this way, there are the centers of spacer hole 22a and cover hole 23a along the center axis of blood storing part 24, and the center of substrate hole 21a is positioned closer to opposite side 24e to supply channel 25. On opposite side 24e, the wall surface of substrate hole 21a and the wall surface of spacer hole 22a are aligned. Further, diameter 21f of substrate hole 21a is greater than diameter 23f of cover hole 23a and diameter 22f of spacer hole 22a is greater than diameter 21f of substrate hole 21a.

Similar to Embodiment 1, in blood storing part 24 of blood sensor 20c, cover 23 projects toward the interior of blood storing part 24 to form projecting part 23c. The length of projection of projecting part 23c (200 micrometers) near supply channel 25 is greater than the sum of the thicknesses of substrate 21 and spacer 22 (150 micrometers). Consequently, similar to Embodiment 1, thanks to projecting part 23c, it is possible to let blood drop 15a sampled in the blood storing part flow into supply channel 25 before reaching the contact point between blood storing part 24 and skin 11.

As shown in FIG. 11B, the width of groove 26b is wider (200 micrometers) on the supply channel 25 side and gradually becomes narrower away from supply channel 25, and there is no groove 26b on opposite side 24e to the supply channel (the width of groove 26b is zero). Therefore, the volume of groove 26b is smaller than groove 26a of blood sensor 20b according to Embodiment 2. Consequently, the amount of blood left in the groove after a test is reduced, so that it is possible to reduce the amount of blood 15 to sample which is required for a test.

Figure 12A:
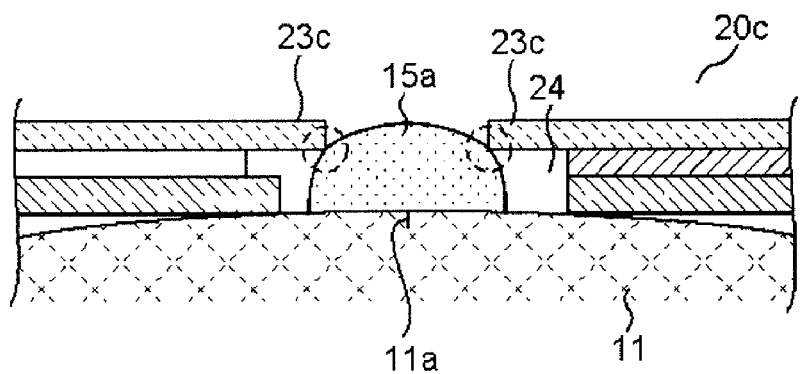
FIG. 12A is a cross-sectional view of the blood storing part of the blood sensor according to Embodiment 3 and shows a state where the drop of blood flowing out from punctured skin contacts the projecting part of the cover hole.
Figure 12B:
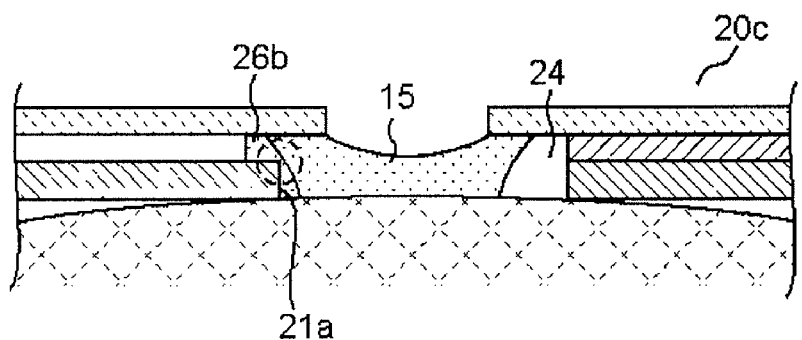
FIG. 12B is a cross-sectional view of the blood storing part of the blood sensor according to Embodiment 3 and shows a state where blood flows into the supply channel from the blood storing part.
Figure 12C:
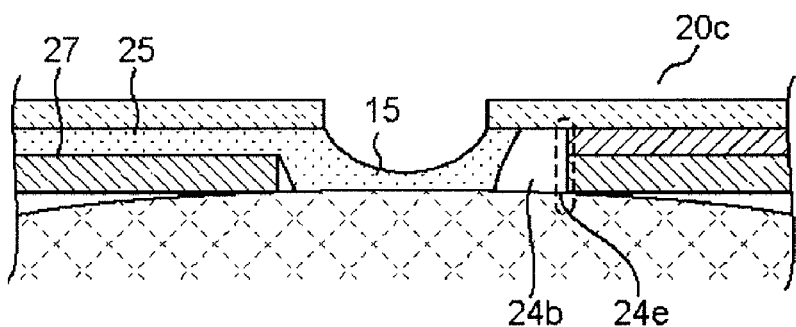
FIG. 12C is a cross-sectional view of the blood storing part of the blood sensor according to Embodiment 3 and shows a state after blood in the blood storing part flows into the supply channel.

The operation of sampling blood by blood sensor 20c will be explained with reference to FIG. 12A to FIG. 12C. When skin 11 inside blood storing part 24 is punctured, blood 15 flows out from punctured hole 11a to form blood drop 15a. As shown in FIG. 12A, when blood drop 15a becomes bigger, blood drop 15a abuts on the tips of projecting part 23c (shown by dotted-line circles). Then, as shown in FIG. 12B, blood drop 15a tries to spread inside blood storing part 24 at a burst. Spreading blood 15 abuts on the tips of substrate hole 21a of the spacer side (see inside the dotted-line circles in FIG. 12B) shown by dotted-lines. Stronger capillary force is produced in groove 26b than in the space formed by projecting part 23c and skin 11. Consequently, as shown in FIG. 12C, blood 15 flows into groove 26b with capillary force, at a burst, and blood 15 that has flowed into groove 26b flows into supply channel 25 in the rate-controlled state. In this way, thanks to groove 26b in which stronger capillary force is produced, it is possible to let blood 15 flow into detecting section 27 through supply channel 25 in a more reliable manner.

As described above, in blood sensor 20c, the center of substrate hole 21a is closer to opposite side 24e to supply channel 25 than the center of cover hole 23a. On the other hand, mostly, the part of the skin to be punctured is almost the same position as the center part of cover hole 23a. According to the positional relationship, naturally, the part of skin to be punctured (the center of the skin from which blood drop 15a exudes) is closer to the supply channel 25 side than the center of substrate hole 21a. Consequently, as shown in FIG. 12C, blood drop 15a is provided mainly on the supply channel 25 side to form vacuum 24b.

Figure 13:
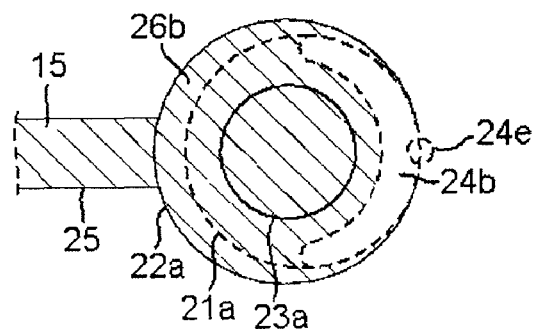
FIG. 13 is a perspective plan view of the blood storing part of the blood sensor according to Embodiment 3 and shows a state after blood in the blood storing part flows into the supply channel.

Further, there is no groove 26b on opposite side 24e to supply channel 25, so that the amount of blood left in groove 26b is less than that of blood sensor 20b according to Embodiment 2. Consequently, it is possible to decrease the amount of blood 15 to sample and reduce burden on patients. FIG. 13 is a perspective plan view of the blood sensor in the state of FIG. 12C. As shown in FIG. 12C and FIG. 13, vacuum 24b, in which blood 15 is not left in blood storing part 24, is formed. Compared to blood sensor 20b according to Embodiment 2, the amount of blood 15 required for a test by blood sensor 20c is reduced by the volume corresponding to vacuum 24b.

Embodiment 4

FIG. 14 and FIG. 15 show blood sensor 20d according to Embodiment 4.

Blood sensor 20d differs from blood sensor 20a according to Embodiment 1 in that projecting part 23c of cover 23 is formed on the supply channel 25 side but not on opposite side 24e to supply channel 25. This difference will be mainly explained below, and the same members as in Embodiment 1 will be assigned the same reference numerals and explanation thereof will be simplified.

Figure 14A:
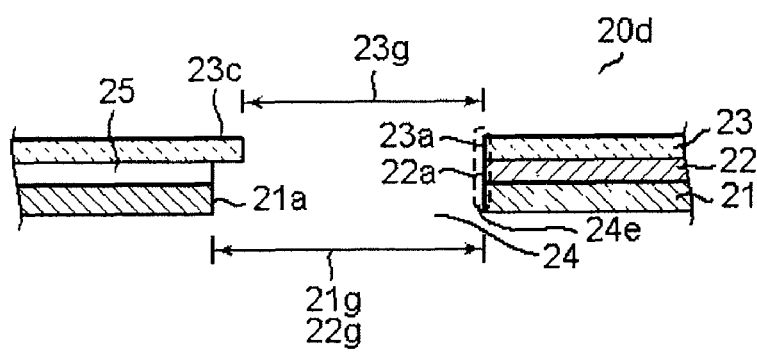
FIG. 14A is a cross-sectional view of the blood storing part of the blood sensor according to Embodiment 4.
Figure 14B:
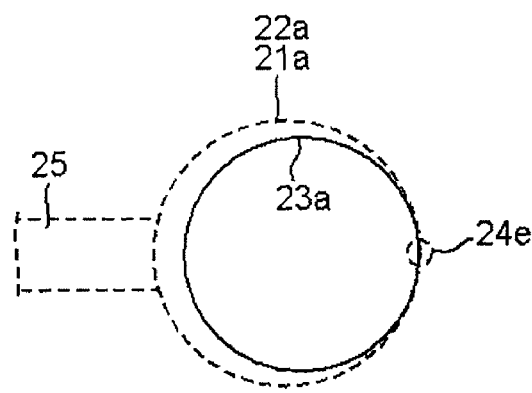
FIG. 14B is a perspective plan view of the blood storing part of the blood sensor according to Embodiment 4.

FIG. 14A is a cross-sectional view of blood storing part 24 of blood sensor 20d and its vicinity and FIG. 14B is its perspective plan view. In FIG. 14A and FIG. 14B, diameter 21g of substrate hole 21a formed in substrate 21 and diameter 22g of spacer hole 22a formed in spacer 22 are each 1.75 millimeters. On the other hand, diameter 23g of cover hole 23a formed in cover 23 is 1.5 millimeters. That is, diameter 21g of substrate hole 21a and diameter 22g of spacer hole 22a are equal, and, on the other hand, diameter 23g of cover hole 23a is smaller than diameter 22g of spacer hole 22a.

Further, the centers of substrate hole 21a and spacer hole 22a are concentric, and the center of cover hole 23a is at a position farther away from supply channel 25 than the center of substrate hole 21a. That is, there are the centers of substrate hole 21a and spacer hole 22a along the center axis of blood storing part 24 and the center of cover hole 23a is positioned on the opposite side to supply channel 25.

Therefore, the wall surfaces of substrate hole 21a, spacer hole 22a and cover hole 23a are aligned on opposite side 24e to supply channel 25 and there is no projection from cover 23. Cover 23 of blood sensor 20d projects from the supply channel 25 side toward the interior of blood storing part 24 to form projecting part 23c. However, cover 23 of blood sensor 20d does not project from opposite side 24e to supply channel 25 toward the interior of blood storing part 24, and no projecting part is formed.

Then, the length of projection of projecting part 23c (250 micrometers) of cover 23 near supply channel 25 is greater than the sum of the thicknesses of substrate 21 and spacer 22 (150 micrometers). Consequently, similar to Embodiment 1, thanks to projecting part 23c, it is possible to let blood drop 15a sampled in blood storing part 24 flow into supply channel 25 before reaching the contact point between blood storing part 24 and skin 11.

Figure 15A:
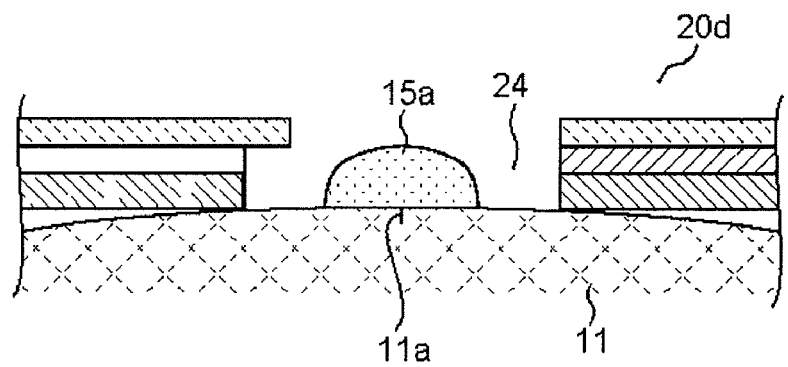
FIG. 15A is a cross-sectional view of the blood storing part of the blood sensor according to Embodiment 4 and shows a state where the drop of blood flowing out from punctured skin is formed.
Figure 15B:
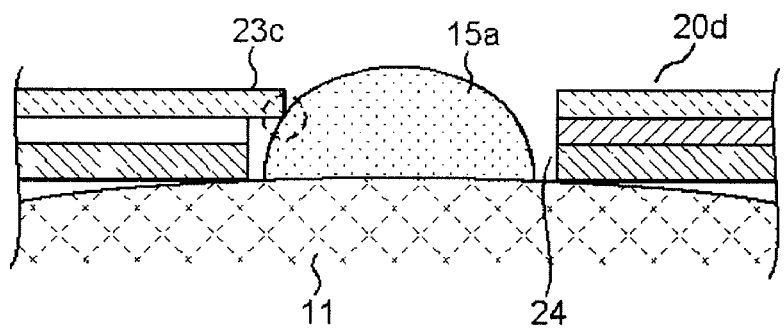
FIG. 15B is a cross-sectional view of the blood storing part of the blood sensor according to Embodiment 4 and shows a state where the drop of blood flowing out from punctured skin contacts the projecting part of the cover hole.
Figure 15C:
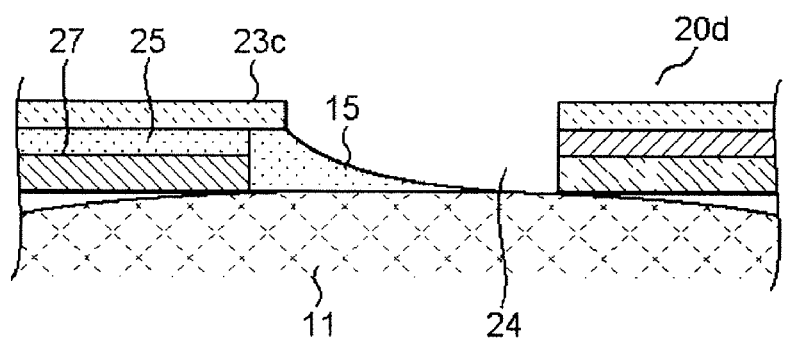
FIG. 15C is a cross-sectional view of the blood storing part of the blood sensor according to Embodiment 4 and shows a state after blood in the blood storing part flows into the supply channel.

The operation of sampling blood by blood sensor 20d will be explained with reference to FIG. 15A to FIG. 15C. As shown in FIG. 15A, when skin 11 inside blood storing part 24 is punctured, blood 15 flows out from punctured hole 11a to form blood drop 15a. When blood drop 15a becomes bigger, blood drop 15a abuts on the tip (see the dotted-line circle) of projecting part 23c as shown in FIG. 15B. Then, as shown in FIG. 15C, thanks to the capillary force produced by projecting part 23c and skin 11, blood drop 15a flows into detecting section 27 at a burst through supply channel 25 in a rate-controlled state.

In blood sensor 20d, space between cover 23 and skin 11 is formed by supply channel 25 and air hole 28 (see FIG. 4) near supply channel 25 and its vicinity to produce capillary force. On the other hand, no space is formed between cover 23 and skin 11 on the opposite side to supply channel 25. Further, before blood 15 fulfills blood storing part 24, blood 15 contacts projecting part 23c of cover 23 provided on the supply channel 25 side. Consequently, little blood 15 flows to the opposite side to the supply channel 25 side, and it is possible to lead blood 15 to detecting section 27 through supply channel 25 in a reliable manner. Accordingly, the amount of blood left in blood storing part 24 becomes less than those of Embodiments 1 to 3. Accordingly, the amount of blood 15 to sample is reduced and burden on the patient is reduced.

Embodiment 5

FIG. 16 and FIG. 17 show blood sensor 20e according to Embodiment 5.

Near supply channel 25, blood sensor 20e has projecting part 23c of cover 23 projecting toward the interior of blood storing part 24. That is, blood sensor 20e differs from blood sensor 20a according to Embodiment 1 in that cover 23 selectively projects near supply channel 25 and no projecting part projecting from the other periphery toward the interior of blood storing part 24 is formed. This difference will be mainly explained below, and the same members as in blood sensor 20a according to Embodiment 1 will be assigned the same reference numerals and explanation thereof will be simplified.

Figure 16A:
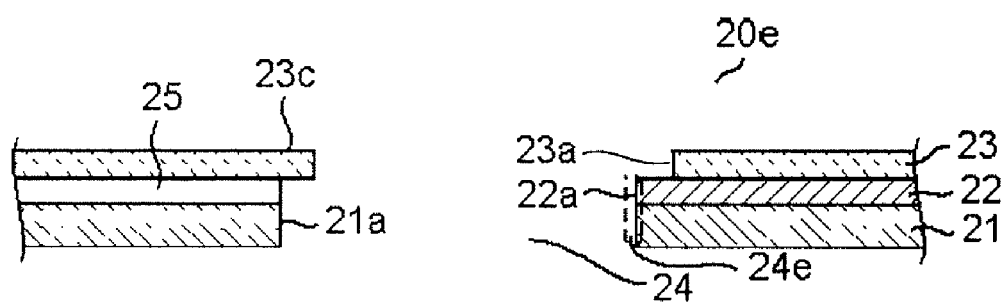
FIG. 16A is a cross-sectional view of the blood storing part of the blood sensor according to Embodiment 5.
Figure 16B:
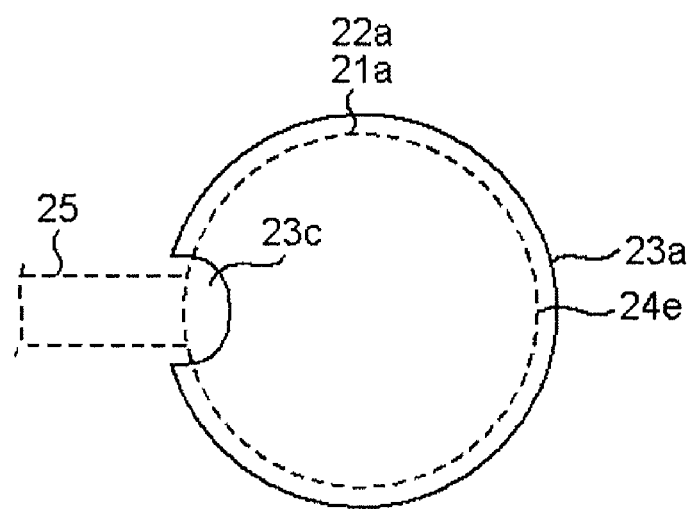
FIG. 16B is a perspective plan view of the blood storing part of the blood sensor according to Embodiment 5.

FIG. 16A is a cross-sectional view of blood storing part 24 of blood sensor 20e and its vicinity and FIG. 16B is its perspective plan view. The wall surfaces of substrate hole 21a and spacer hole 22a of blood sensor 20e are aligned. Cover 23 of blood sensor 20e has a projection portion projecting only from the supply channel 25 side toward the interior of blood storing part 24, to form projecting part 23c. On the other hand, cover 23 does not have a projection portion other than projecting part 23c and does not project except from the supply channel 25 side (including opposite side 24e). The wall surface of cover hole 23a of blood sensor 20e is recessed away from blood storing part 24 on opposite side 24e, compared to the wall surfaces of substrate hole 21a and spacer hole 22a. It naturally follows that wall surface 23a of cover hole 23 may be aligned with the wall surfaces of substrate hole 21a and spacer hole 22a on opposite side 24e.

Further, the length of projection of projecting part 23c (250 micrometers) of cover 23 near supply channel 25 is greater than the sum of thicknesses of substrate 21 and spacer 22 (150 micrometers). Consequently, similar to Embodiment 1, thanks to projecting part 23c, it is possible to let blood drop 15a sampled in blood storing part 24 flow into supply channel 25 before reaching the contact point between blood storing part 24 and skin 11.

Figure 17A:
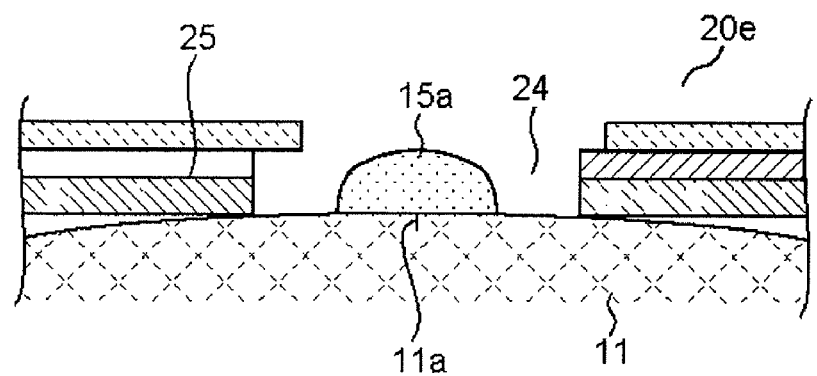
FIG. 17A is a cross-sectional view of the blood storing part of the blood sensor according to Embodiment 5 and shows a state where the drop of blood flowing out from punctured skin is formed.
Figure 17B:
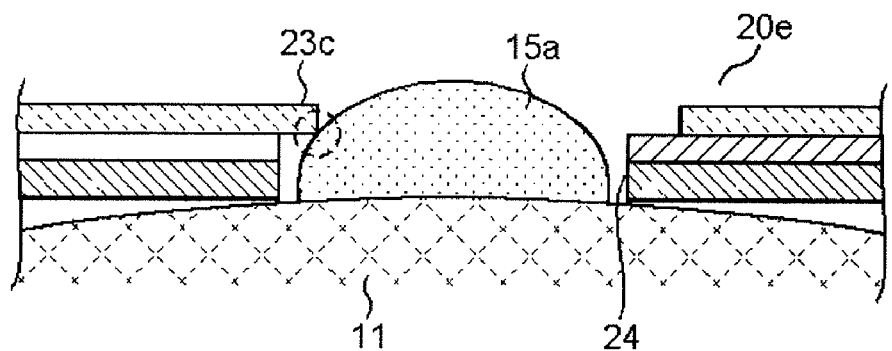
FIG. 17B is a cross-sectional view of the blood storing part of the blood sensor according to Embodiment 5 and shows a state where the drop of blood flowing out from punctured skin contacts a projecting part of the cover hole.
Figure 17C:
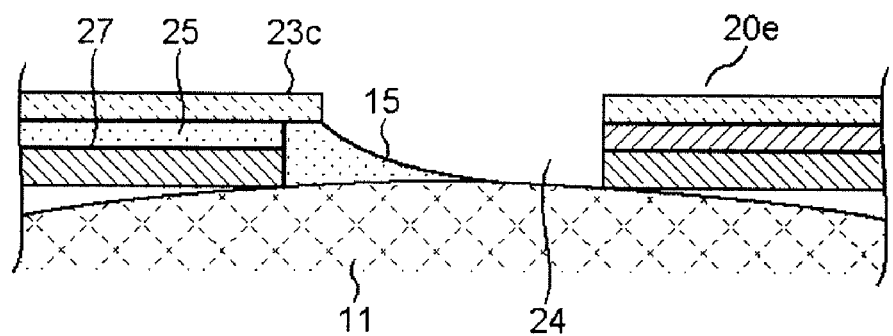
FIG. 17C is a cross-sectional view of the blood storing part of the blood sensor according to Embodiment 5 and shows a state after blood in the blood storing part flows into the supply channel.

The operation of sampling blood by blood sensor 20e will be explained with reference to FIG. 17A to FIG. 17C. As shown in FIG. 17A, when skin inside blood storing part 24 is punctured, blood 15 flows out from punctured hole 11a to form blood drop 15a. As shown in FIG. 17B, when blood drop 15a becomes bigger, blood drop 15a abuts on the tip of projecting part 23c (see dotted-line circle). Then, as shown in FIG. 17C, thanks to the capillary force produced in space between projecting part 23c and skin 11, blood drop 15a flows into detecting section 27 at a burst through supply channel 27 in a rate-controlled state.

In this way, although blood sensor 20e selectively has a projecting part of cover 23 near the supply channel, blood sensor 20e makes it possible to let blood 15 flow into detecting section 27 through supply channel 25 in a reliable manner before blood 15 fulfills blood storing part 24 as in blood sensor 20d.

Further, part of cover 23 of blood sensor 20e near supply channel 25 selectively projects toward the interior of blood storing part 24. Accordingly, as in above-described Embodiments 3 and 4, blood 15 is less likely to reach the entire periphery of the inner wall surface in blood storing part 24. Blood drop 15a contacts only the portion of projecting part 23c of cover 23 of blood sensor 20e and is led to supply channel 25 by capillary force. Blood stored in the blood storing part can be utilized without waste, and only the small amount of blood to sample is sufficient and, consequently, it is possible to alleviate pain upon a test.

2. The blood test apparatus according to the present invention.

The features of the blood test apparatus according to the present invention include having the above-described blood sensor. Further, the blood sensor is preferably made as a cartridge to be attached to the blood test apparatus removably. An example of the blood test apparatus according to the present invention will be explained below.

Embodiment 6

FIG. 18 to FIG. 23 show blood test apparatus 40 according to Embodiment 6. Blood sensor 20 (any one of blood sensors 20a to 20e) explained in Embodiments 1 to 5 is attached to blood test apparatus 40.

Figure 18:
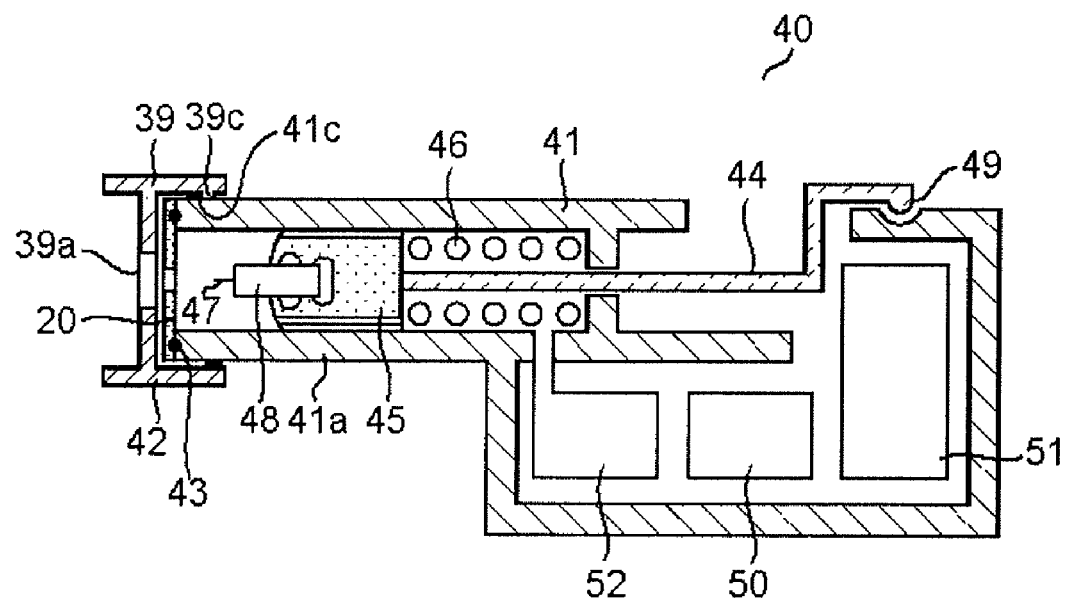
FIG. 18 is a cross-sectional view of the blood test apparatus according to Embodiment 6 using a puncturing needle as puncturing means.

FIG. 18 is a cross-sectional view of blood test apparatus 40. One end of housing 41 made of resin forms cylinder body 41a of a cylindrical shape. Cartridge 42 is inserted removably in the tip of cylinder body 41a to be attached.

Cartridge 42 attached removably is composed of cylindrical holder 39 and blood sensor 20 attached inside holder 39. Holder 39 forming cartridge 42 is preferably formed of a transparent member such that blood sampling can be visually checked. Further, in holder 39 facing the blood storing part of blood sensor 20, window 39a through which the puncturing member (puncturing needle 47 or laser light) penetrates is formed.

Inside cylinder body 41a, plunger 45 to which handle 44 is coupled is provided slidably. Plunger 45 is biased toward cartridge 42 by spring 46. Further, lancet 48 attached with puncturing needle 47 is attached to plunger 45 detachably.

Handle 44 is extended to the outside of housing 41 and engaged with engaging part 49. By releasing engagement by engaging part 49, puncturing needle 47 penetrates the blood storing part of blood sensor 20 and punctures skin. The puncturing means is formed of handle 44, plunger 45, spring 46, puncturing needle 47 and lancet 48.

Electrical circuit section 50 provided inside housing 41 is connected with six connectors 43 (43a to 43f). Power is supplied to electrical circuit section 50 from battery 51. Negative pressure means 52 can apply a negative pressure near blood sensor 20 to apply a negative pressure to the interior of the blood storing part through the cover hole.

Figure 19:
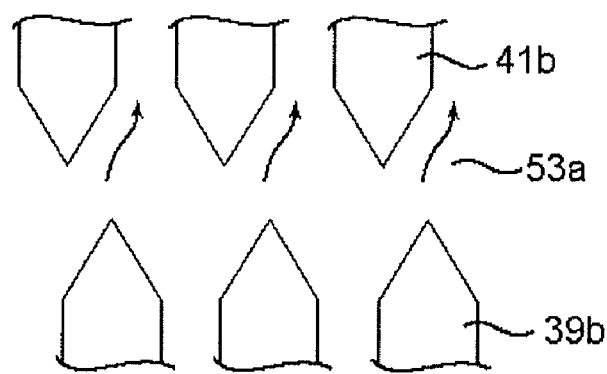
FIG. 19 is a schematic view of an attaching part when a cartridge forming the blood test apparatus according to Embodiment 6 is attached.

FIG. 19 shows the state where cartridge 42 is attached to cylinder body 41a.

Guides 39b of a convex shape are formed inside holder 39 of cartridge 42 and guides 41b of a convex shape are formed outside cylinder body 41a. FIG. 19 shows the state where guides 39b and guides 41b mesh with each other and cartridge 42 is attached to cylinder body 41a. When cartridge 42 is attached to cylinder body 41a, guides 39b are guided along arrow 53a, so that the rotational angle of cartridge 42 that designates the direction of attachment as the rotational axis is adjusted. Consequently, when the rotational angle that designates the direction of attachment as the rotational axis is not adjusted when cartridge 42 is attached, connection electrodes 31a to 35a and reference electrode 33c formed in blood sensor 20 of cartridge 42 are reliably connected with connectors 43 (43a to 43f) formed in cylinder body 41a.

When cartridge 42 is attached to cylinder body 41a, positioning concave part 41c (see FIG. 18) provided in cylinder body 41a meshes with positioning convex part 39c provided in holder 39. By this means, cartridge 42 is fixed to a predetermined position of cylinder body 41a. Consequently, it is possible to keep constant the depth of puncturing of the skin by the puncturing means.

Figure 20:
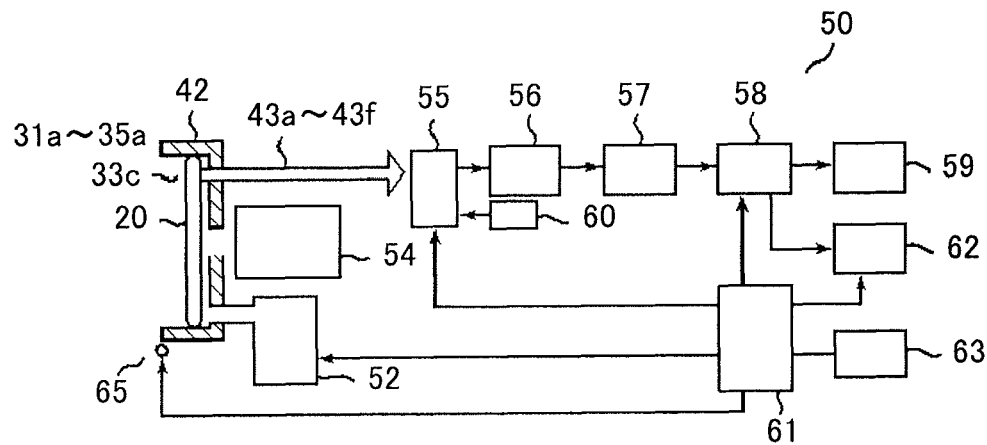
FIG. 20 is a block diagram of an electrical circuit section forming the blood test apparatus according to Embodiment 6.

FIG. 20 is a block diagram of electrical circuit section 50. In FIG. 20, connection electrodes 31a to 35a and reference electrode 33c of blood sensor 20 are connected with switch circuit 55 through connectors 43a to 43f. The output of switch circuit 55 is connected with the input of current/voltage converter 56. The output of current/voltage converter 56 is connected with the input of calculating section 58 through analogue/digital converter (hereinafter, "A/D converter") 57. The output of calculating section 58 is connected with display section 59 formed of liquid crystal. Reference voltage source 60 is connected with switch circuit 55. Reference voltage source 60 may be a ground potential.

The output of controlling section 61 is connected with a controlling terminal of switch circuit 55, calculating section 58, timer 63, negative pressure means 52 and skin detection sensor 65. The output of controlling section 61 is also connected with the input of transmitting section 62. When skin detection sensor 65 detects a contact with skin, it is possible to make puncturing means 54 automatically puncture skin. It naturally follows that it may also be possible to make puncturing means 54 puncture skin by a manual button without arranging skin detection sensor 65. Puncturing means 54 is provided facing blood storing part 24 of blood sensor 20.

Next, the operation of electrical circuit section 50 will be explained.

To perform a blood test, to which connectors 43a to 43f connection electrodes 31a to 35a and reference electrode 33c are connected is specified first. According to commands from controlling section 61, connectors of the electrical resistance of zero between adjacent connectors are specified among connectors 43a to 43f. Connector 43 to be connected with reference electrode 33c, which is an electrode connected with a connector of the electrical resistance of zero, is determined. Based on a connector connected with reference electrode 33c, connectors 43 to be sequentially connected with connection electrodes 34a, 35a, 31a, 32a and 33a are specified. In this way, connectors 43a to 43f connected with connection electrodes 31a to 35a and reference electrode 33c are specified.

Next, blood is sampled to perform a test. By switching switch circuit 55, detection electrode 31 which is an active electrode for measuring the amount of blood components, is connected with current/voltage converter 56. Further, detection electrode 32 which is a sensing electrode for sensing an inflow of blood 15 is connected with reference voltage source 60. Then, a constant voltage is applied between detection electrode 31 and detection electrode 32. In this state, when blood flows in, a current flows between detection electrode 31 and detection electrode 32. This current is converted into the voltage by current/voltage converter 56, the value of this voltage is converted into a digital value by A/D converter 57. Then, this digital value is outputted to calculating section 58. Calculating section 58 senses that blood 15 flows in sufficiently, based on this digital value. At this point, the operation of negative pressure means 52 is stopped.

Next, blood components (for example, glucose) are measured. To measure glucose content, first, switch circuit 55 is switched according to commands from controlling section 61, and detection electrode 31, which is an active electrode for measuring the glucose content, is connected with current/voltage converter 56. Further, detection electrode 33, which is a counter electrode for measuring glucose component content, is connected with reference voltage source 60.

When the glucose in blood and its glucose oxidation-reduction enzyme are reacted for a certain period, during the reaction, current/voltage converter 56 and reference voltage source 60 are turned off. After a certain period (1-10 seconds) passes, a certain voltage (0.2 to 0.5 V) is applied between detection electrode 31 and detection electrode 33 according to the commands of controlling section 61. Then, a current flows between detection electrode 31 and detection electrode 33. This current is converted into the voltage by current/voltage converter 56, and the voltage value is converted into a digital value by A/D converter 57 and is outputted toward calculating section 58. Calculating section 58 converts this digital value to glucose content.

After the glucose content is measured, an Hct value is measured. To measure the Hct value, first, switch circuit 55 is switched according to commands from controlling section 61. Then, detection electrode 35, which is the active electrode for measuring the Hct value, is connected with current/voltage converter 56. Further, detection electrode 31, which is the counter electrode for measuring the Hct value, is connected with reference voltage source 60.

Next, according to the commands from controlling section 61, a certain voltage (2V to 3V) is applied between detection electrode 35 and detection electrode 31 by current/voltage converter 56 and reference voltage source 60. The current flowing between detection electrode 35 and detection electrode 31 is converted into the voltage by current/voltage converter 56 and the voltage value is converted into a digital value by A/D converter 57. The digital value is outputted to calculating section 58 and calculating section 58 converts this digital value into an Hct value.

By using the Hct value and glucose content resulting from measurement and referring to a calibration curve or calibration curve table determined in advance, glucose content is corrected by the Hct value and the correction result is displayed in display section 59. Further, the correction result is transmitted from transmitting section 62 to the injection apparatus that injects insulin. Although a radio wave may be used for this transmission, transmission is preferably performed by optical communication that does not interfere with medical equipment.

When the dose of insulin to administer is automatically set by transmitting corrected measurement data from transmitting section 62 in this way, setting the dose of insulin to be administered by the patient is not required, which eliminates botheration. Further, the dose of insulin can be set in the injection apparatus without an artificial means, so that it is possible to avoid setting error.

Although the blood test apparatus according to Embodiment 5 has been explained as a glucose measuring apparatus, the blood test apparatus is appropriated to measure blood components other than glucose such as lactate acid or cholesterol levels.

Figure 21:
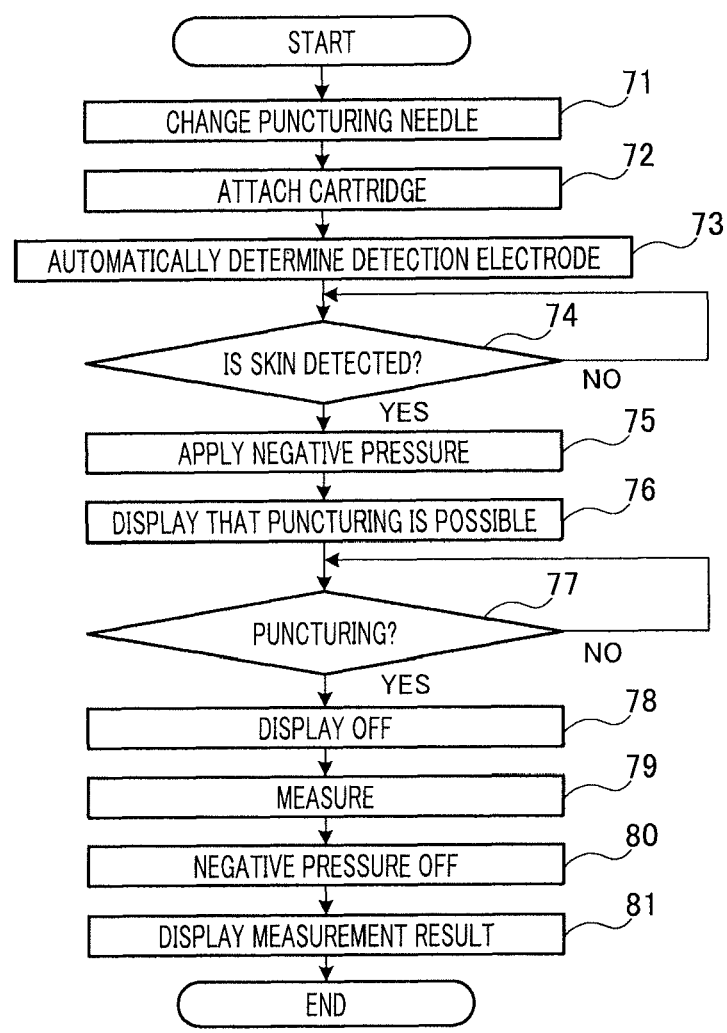
FIG. 21 is a flowchart of a blood test using the blood test apparatus according to Embodiment 6.

Next, a test flow by blood test apparatus 40 will be explained using FIG. 21.

In step 71, lancet 48, to which puncturing needle 47 is attached, is attached to plunger 45. Next, in step 72, cartridge 42, in which blood sensor 20 is attached, is attached to an opening tip part of cylinder body 41a.

In step 73, a power switch of blood test apparatus 40 is turned on by a manual operation or automatically by attaching cartridge 42. Power is supplied from battery 51 to electrical circuit section 50. When power is supplied to power circuit section 50, reference electrode 33c of blood sensor 20 is detected first. Detection electrodes 31 to 35 are specified based on detected reference electrode 33c.

In step 74, stand-by continues until cartridge 42 of blood test apparatus 40 is adequately set to skin 11 to be punctured. When skin detecting sensor 65 of cartridge 42 detects a contact with skin 11, the flow proceeds to step 75 to operate negative pressure means 52. Instead of arranging skin detecting sensor 65, controlling section 61 may operate negative pressure means 52 by operating negative pressure button 64 (not shown) manually. Negative pressure means 52 applies a negative pressure near blood sensor 20.

When the current in the vacuum pump forming negative pressure means 52 changes or the time determined by timer 63 in advance passes, it is decided that skin inside blood storing part 24 has been sufficiently lifted up by the negative pressure, and the flow proceeds to step 76.

In step 76, display section 59 displays that puncturing is possible. In next step 77, according to this display, the patient releases an engagement of engaging part 49 of handle 44 and punctures skin 11 by puncturing needle 47. Blood 15 flows out from punctured skin 11. Outflowing blood 15 is stored in blood storing part 24 and is further led to detecting section 27 of blood sensor 20. In step 79, the blood sugar level of blood 15 is measured.

After the blood sugar level is measured in step 79, the flow proceeds to step 80 and negative pressure means 52 stops. In step 81, the blood sugar level measured is displayed in display section 59. Display on display section 59 in step 76 (displaying that "puncturing is possible") is stopped at the timing which blood 15 reaches detection electrode 32, before performing measurement in step 79 (step 78). Further, the negative pressure may be stopped at the same time when displaying is stopped.

Figure 22:
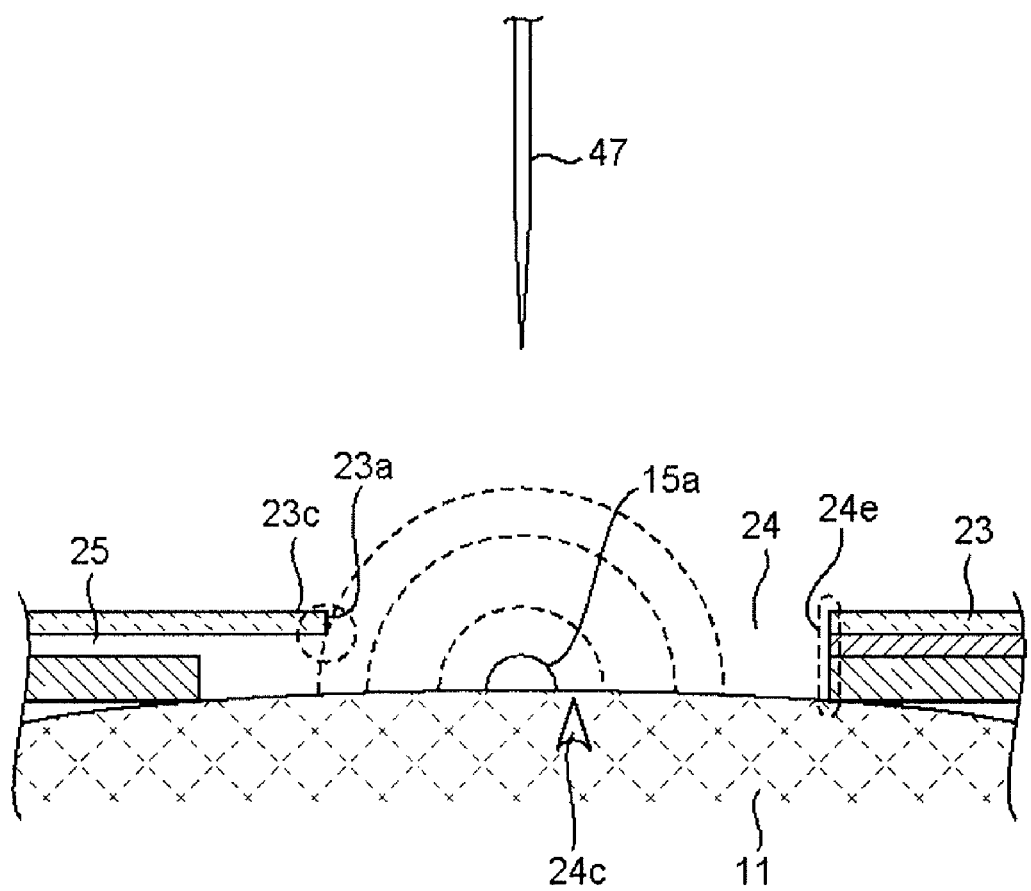
FIG. 22 is a cross-sectional view of the blood storing part of the blood sensor in the blood test apparatus according to Embodiment 6 and shows the part to be punctured.

Upon puncturing of skin 11 using blood test apparatus 40, the position of skin to be punctured by the puncturing needle of puncturing means 54 is preferably a position closer to supply channel 25 than center 24c of cover hole 23a inside blood storing part 24 as shown in FIG. 22. In this way, by puncturing the position closer to supply channel 25 than center 24c of cover hole 23a, blood drop 15a abuts on projecting part 23c before abutting on opposite side 24e in blood storing part 24. Consequently, it is possible to let blood 15 flow into supply channel 25 efficiently, in a reliable manner.

Figure 23:
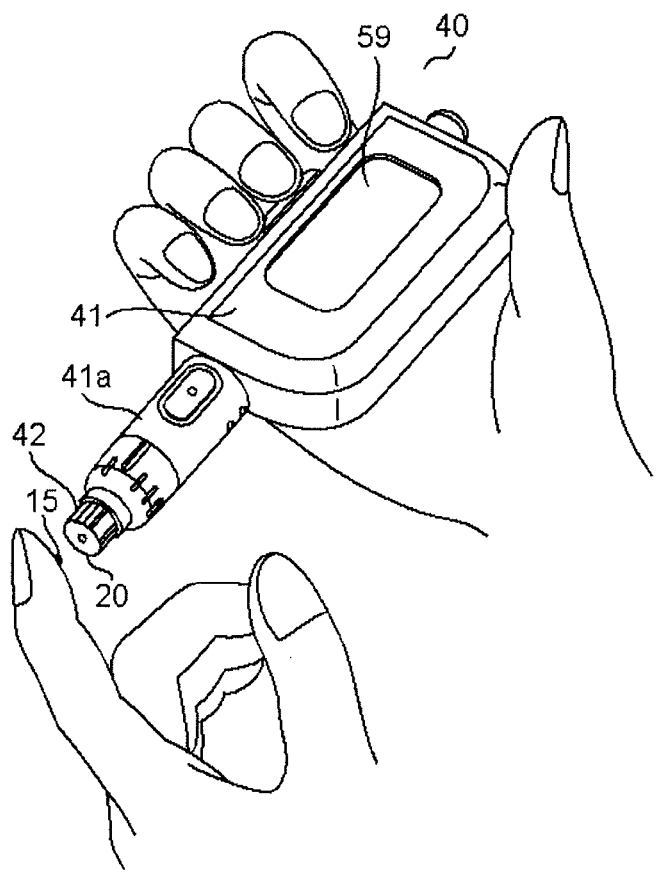
FIG. 23 shows a state where a patient uses the blood test apparatus according to Embodiment 6.

FIG. 23 shows a state where the patient holds blood test apparatus 40 with the right hand and samples blood 15 from the forefinger of the left hand, to test the blood sugar level. One end of housing 41 is coupled to housing 41a. Cartridge 42 is attached to housing 41a and blood sensor 20 is attached to one end of cartridge 42. Further, display section 59 is provided on one side of housing 41.

Embodiment 7

Figure 24:
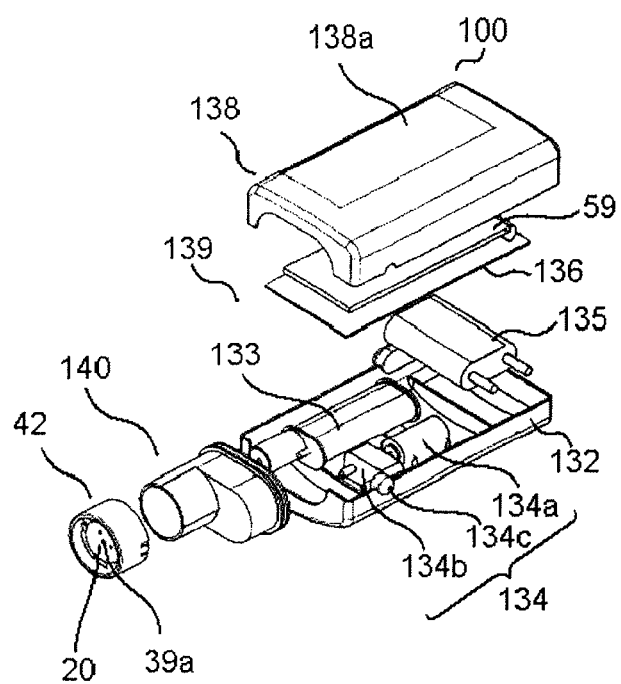
FIG. 24 is an exploded perspective view of the blood test apparatus according to Embodiment 7 using laser as puncturing means.

FIG. 24 is an exploded perspective view of blood test apparatus 100 according to Embodiment 7. Blood test apparatus 100 are the same as blood test apparatus 40 explained in Embodiment 6 except that laser emitting apparatus 133 is used as the puncturing means. This difference will be described here, and the same members will be assigned the same reference numerals and explanation thereof will be simplified.

In FIG. 24, lower case 132 accommodates: laser emitting apparatus 133 as the puncturing means; suction pump 134a forming negative pressure means 134; pump valve unit 134b; vent switch 134c; battery 135 for supplying power to electrical components; electrical circuit section 136 attached on these components; and display section 59 that is attached on electrical circuit section 136 and that is formed of liquid crystal. Lower case 132 in which these components are attached is covered by upper case 138 to form body 139. In upper case 138, transparent display window 138a is provided at a position meeting display section 59.

The operation of electrical circuit section 136 is the same as the circuit of electrical circuit section 50 used in blood test apparatus 40. However, electrical circuit section 136 differs from electrical circuit section 50 in that, in blood test apparatus 100, a puncturing button and laser emitting apparatus 133 that emits laser light by pressing down the puncturing button are connected with controlling section 61.

Adaptor 140 connects body 139 and cartridge 42 and one end of adaptor 140 is attached to body 139. The other end of adaptor 140 forms a cylinder body of a cylindrical shape to which cartridge 42 is attached removably. Blood sensor 20 is attached inside cartridge 42. Window 39a is provided at the center of holder 39 forming cartridge 42 and is on the laser radiating axis through which laser light from laser emitting apparatus 133 passes.

The puncturing means of blood test apparatus 100 according to Embodiment 7 is not a puncturing needle but laser emitting apparatus 133, so that it is not necessary to change the puncturing means. Consequently, a changing operation is eliminated, which facilitates a blood test. Further, laser emitting apparatus 133 makes it possible to puncture skin of a patient in non-contact without using a puncturing needle directly touching the skin of the patient, which is sanitary. Further, there are no moving components in terms of mechanism, so that there is little malfunction and the reliability increases. Further, puncturing is performed in non-contact, so that blood test apparatus 100 can be subjected to water-proof treatment at ease and can be washed entirely.

Cartridge 42 in blood test apparatus 100 using laser emitting apparatus 133 may be used in common with the cartridge of blood test apparatus 40 using puncturing needle 47 according to Embodiment 6. That is, cartridge 42 can be used both in blood test apparatus 40 and blood test apparatus 100.

INDUSTRIAL APPLICABILITY

The blood sensor according to the present invention enables a precise test with a small amount of blood. Consequently, the blood test apparatus using the blood sensor according to the present invention is useful for medical equipment in particular.

The present invention claims priority based on Japanese Patent Application No. 2006-252075, filed on Sep. 19, 2006. The disclosure including the specification and drawings as filed, is incorporated herein by reference in its entirety.

The invention claimed is:
1. A blood sensor comprising:
a substrate;
a spacer that is configured to be attached on an upper surface of the substrate;
a cover that is configured to be attached on an upper surface of the spacer;
a blood storage that comprises a substrate hole in the substrate, a part of a spacer hole in the spacer and which is configured to be coupled to the substrate hole, and a cover hole which is in the cover and which is configured to be coupled to the spacer hole;
a supply channel comprises another part of the spacer hole and that extends away from the blood storage and is configured to communicate with the blood storage; and
a plurality of detection electrodes on the supply channel,
wherein at least a portion of the edge of the cover hole extends from a supply channel side toward an interior of the blood storage, beyond the edge of the spacer hole and the edge of the substrate hole.
2. The blood sensor according to claim 1, wherein a length of the projection of the cover is greater than a sum of a thickness of the substrate and a thickness of the spacer.
3. The blood sensor according to claim 1, wherein an open area of the cover hole is equal to or less than an open area of the substrate hole and is smaller than an open area of the spacer hole.
4. The blood sensor according to claim 1, wherein at least a portion of the edge of the substrate hole extends from the supply channel side toward the interior of the blood storage, beyond the edge of the spacer hole and is configured to define a space between the substrate and the cover.
5. The blood sensor according to claim 1, wherein:
the substrate hole, the spacer hole of the blood storage, and the cover hole are round;
a diameter of the cover hole is equal to or less than a diameter of the substrate hole and is smaller than a diameter of the spacer hole; and
the centers of the substrate hole, the spacer hole and the cover hole are concentric with each other.
6. The blood sensor according to claim 1, wherein:
the substrate hole, the spacer hole of the blood storage, and the cover hole are round;
a diameter of the cover hole is equal to or less than a diameter of the substrate hole and is smaller than a diameter of the spacer hole;
a centers of the cover hole and the spacer hole are concentric with each other; and
the center of the substrate hole is farther from the supply channel than the center of the spacer hole.
7. The blood sensor according to claim 1, wherein:
the substrate hole, the spacer hole of the blood storage, and the cover hole are round;
a diameter of the substrate hole is larger than a diameter of the cover hole and equal to a diameter of the spacer hole;
centers of the substrate hole and the spacer hole are concentric with each other; and the center of the cover hole is farther away the supply channel than the center of the substrate hole.

8. The blood sensor according to claim 1, wherein the cover comprises a projection configured to project from the supply channel side toward the interior of the blood storage.

9. The blood sensor according to claim 1, wherein the blood storage is configured to have a negative pressure applied thereto through the cover hole.

10. The blood sensor according to claim 1, wherein:
the substrate, the spacer and the cover comprise a base plate of a polygon;
electrodes are at apexes of the polygon;
the electrodes at the apexes are each configured to be connected with one of the plurality of detection electrodes; and
two of the electrodes at the apexes are connected with the same detection electrode.

11. The blood sensor according to claim 10, wherein the base plate is a regular hexagon.

12. The blood sensor according to claim 1, wherein:
an upper surface of the cover is water-repellent;
an inner surface of the supply channel is hydrophilic; and
a ceiling of the blood storage is less water-repellent than the upper surface of the cover or is less hydrophilic than the inner surface of the supply channel.

13. The blood sensor according to claim 1, wherein a lower surface of the substrate is water-repellent.

14. A blood test apparatus comprising:
a housing;
a cylindrical body at one end of the housing;
a plunger configured to move back and forth inside the cylindrical body;
a lancet that is configured to be detachably held at one end by the plunger and at the other end, is configured to have a puncturing needle attached;
a blood sensor that faces the puncturing needle; and
an electrical circuit that is configured to be connected with the blood sensor,
wherein the blood sensor comprises the blood sensor according to claim 1.

15. The blood test apparatus according to claim 14, wherein:
the blood sensor is configured to be attached to a cylindrical holder to comprise a cartridge; and
the cartridge is configured to be removably attached to the cylindrical body.

16. The blood test apparatus according to claim 15, wherein the holder comprises a transparent or semitransparent member such that an interior of the holder is visible.

17. The blood test apparatus according to claim 14, further comprising negative pressure applier that configured to apply a negative pressure near the blood sensor.

18. The blood test apparatus according to claim 14, wherein the puncturing needle is configured to puncture a skin at a position closer to a supply channel side than the center of a cover hole of the blood sensor.

19. A blood test apparatus comprising:
a housing;
a cylinder body at one end of the housing;
a laser emitting apparatus that is inside the cylinder body;
a blood sensor that is configured to face a laser emitting opening of the laser emitting apparatus; and
an electrical circuit that is configured to be connected with the blood sensor,
wherein the blood sensor comprise the blood sensor according to claim 1.

20. The blood test apparatus according to claim 19, wherein:
the blood sensor is configured to be attached to a cylindrical holder to comprise a cartridge; and
the cartridge is configured to be removably attached to the cylinder body.

21. The blood test apparatus according to claim 20, wherein the holder comprises a transparent or semitransparent member such that an interior of the holder is visible.

22. The blood test apparatus according to claim 19, further comprising a negative pressure applier that is configured to apply a negative pressure near the blood sensor.

23. The blood test apparatus according to claim 19, wherein a laser light that is configured to puncture a skin at a position closer to a supply channel side than the center of a cover hole of the blood sensor.

* * * * *